US007662776B2

(12) United States Patent
Khan et al.

(10) Patent No.: US 7,662,776 B2
(45) Date of Patent: Feb. 16, 2010

(54) TREATMENT OF TUMORS USING SHORT PEPTIDES FROM HUMAN CHORIONIC GONADOTROPIN (HCG)

(75) Inventors: Nisar A. Khan, Rotterdam (NL); Robbert Benner, Barendrecht (NL); Gert Wensvoort, Koekange (NL)

(73) Assignee: Biotempt B.V., Koekange (NL)

( * ) Notice: Subject to any disclaimer, the term of this patent is extended or adjusted under 35 U.S.C. 154(b) by 0 days.

(21) Appl. No.: 11/481,423

(22) Filed: Jul. 5, 2006

(65) Prior Publication Data

US 2007/0021347 A1 Jan. 25, 2007

Related U.S. Application Data

(60) Provisional application No. 60/696,657, filed on Jul. 5, 2005.

(51) Int. Cl.
*A61K 38/04* (2006.01)
(52) U.S. Cl. .......................................... 514/2; 530/330
(58) Field of Classification Search ........................ None
See application file for complete search history.

(56) References Cited

U.S. PATENT DOCUMENTS

| | | | |
|---|---|---|---|
| 4,330,466 A | 5/1982 | Yanaihara et al. |
| 4,427,660 A | 1/1984 | Schiffman et al. |
| 4,571,336 A | 2/1986 | Houck et al. |
| 4,753,965 A | 6/1988 | Stemerick et al. |
| 4,855,285 A | 8/1989 | Stevens |
| 4,966,848 A | 10/1990 | Smith et al. |
| 4,977,244 A | 12/1990 | Muchmore et al. |
| 5,002,961 A | 3/1991 | Dage et al. |
| 5,010,175 A | 4/1991 | Rutter et al. |
| 5,055,447 A | 10/1991 | Palladino et al. |
| 5,102,393 A | 4/1992 | Sarnoff et al. |
| 5,223,397 A | 6/1993 | Pouletty |
| 5,223,421 A | 6/1993 | Smith et al. |
| 5,308,834 A | 5/1994 | Scott et al. |
| 5,380,668 A | 1/1995 | Herron |
| 5,436,270 A | 7/1995 | Wang |
| 5,677,275 A | 10/1997 | Lunardi-Iskandar et al. |
| 5,700,781 A | 12/1997 | Harris |
| 5,801,193 A | 9/1998 | Ojo-Amaize et al. |
| 5,837,218 A | 11/1998 | Peers et al. |
| 5,837,478 A | 11/1998 | Gallatin et al. |
| 5,851,997 A | 12/1998 | Harris |
| 5,854,004 A | 12/1998 | Czernilofsky et al. |
| 5,856,440 A | 1/1999 | Wang |
| 5,877,148 A | 3/1999 | Lunardi-Iskandar et al. |
| 5,942,494 A | 8/1999 | Ginsberg et al. |
| 5,958,413 A | 9/1999 | Anagnostopulos et al. |
| 5,966,712 A | 10/1999 | Sabatini et al. |
| 5,968,513 A | 10/1999 | Gallo et al. |
| 5,972,924 A | 10/1999 | Keep et al. |
| 5,981,486 A | 11/1999 | Matsushima et al. |
| 5,994,126 A | 11/1999 | Steinman et al. |
| 5,997,871 A * | 12/1999 | Gallo et al. ............. 424/185.1 |
| 6,022,696 A | 2/2000 | Harding et al. |
| 6,051,596 A | 4/2000 | Badger |
| 6,075,150 A | 6/2000 | Wang et al. |

(Continued)

FOREIGN PATENT DOCUMENTS

DE 3715662 11/1987

(Continued)

OTHER PUBLICATIONS

Capizzi (Investigational New Drugs, 1996, 14:249-256).*
Albini et al., "Old drugs as novel angiogenesis inhibitors: Preclinical studies with NAC, hCG, EGCG and somatostatin," Clinical & Experimental Metastasis, 1999, pp. 739, vol. 17.
Blackwell et al., "The Role of Nuclear Factor-kB in Cytokine Gene Regulation," Am. J. Respir. Cell Mol. Biol., 1997, pp. 3-9, vol. 17.
Christman et al., "Nuclear factor kappaB: a pivotal role in the systemic inflammatory response syndrome and new target for therapy," Intens Care Med, 1998, pp. 1131-1138, vol. 24.

(Continued)

*Primary Examiner*—Laura B Goddard
(74) *Attorney, Agent, or Firm*—TraskBritt

(57) ABSTRACT

Where it was generally thought that the smallest breakdown products of proteins had no specific biological function on their own, it now emerges that the body may utilize the normal process of proteolytic breakdown to generate important compounds such as gene-regulatory or anti-tumor compounds. Such anti-tumor compounds are useful for the treatment or prevention of tumors and can be used as part of a pharmaceutical composition. The invention provides a pharmaceutical composition for the treatment of a subject suffering from or believed to be suffering from a tumor, said pharmaceutical composition comprising: a therapeutically effective amount of anti-tumor peptide or a functional analogue or derivative thereof together with a pharmaceutically acceptable diluent, wherein the peptide is preferably selected from the group VVC, LAG, AQG, LQGV (SEQ ID NO:1), QVVC (SEQ ID NO:), MTRV (SEQ ID NO:6), AQGV (SEQ ID NO:2), LAGV (SEQ ID NO:3), LQAV (SEQ ID NO:7), PGCP (SEQ ID NO:8), VGQL (SEQ ID NO:9), RVLQ (SEQ ID NO:10), EMFQ (SEQ ID NO:11), AVAL (SEQ ID NO:12), FVLS (SEQ ID NO:13), NMWD (SEQ ID NO:14), LCFL (SEQ ID NO:15), FSYA (SEQ ID NO:16), FWVD (SEQ ID NO:17), AFTV (SEQ ID NO:18), LGTL (SEQ ID NO:19), QLLG (SEQ ID NO:20), YAIT (SEQ ID NO:21), APSL (SEQ ID NO:22), ITTL (SEQ ID NO:23), QALG (SEQ ID NO:24), GVLC (SEQ ID NO:25), NLIN (SEQ ID NO:26), SPIE (SEQ ID NO:27), LNTI (SEQ ID NO:28), LHNL (SEQ ID NO:29), CPVQ (SEQ ID NO:30), EVVR (SEQ ID NO:31), MTEV (SEQ ID NO:32), EALE (SEQ ID NO:33), TLAVE (SEQ ID NO:38), VEGNL (SEQ ID NO:39), LNEAL (SEQ ID NO:40), VLPALP (SEQ ID NO:4), MGGTWA (SEQ ID NO:41), LTCDDP (SEQ ID NO:42), VLPALPQ (SEQ ID NO:43), VCNYRDV (SEQ ID NO:44), CPRGVNP (SEQ ID NO:45), QPLAPLVG (SEQ ID NO:46) or DINGFLPAL (SEQ ID NO:47).

6 Claims, 6 Drawing Sheets

U.S. PATENT DOCUMENTS

| | | | |
|---|---|---|---|
| 6,086,918 A | 7/2000 | Stern et al. |
| 6,150,500 A | 11/2000 | Salerno |
| 6,207,145 B1 | 3/2001 | Tovey |
| 6,235,281 B1 | 5/2001 | Stenzel et al. |
| 6,271,199 B2 | 8/2001 | Brand et al. |
| 6,278,794 B1 | 8/2001 | Parekh et al. |
| 6,309,822 B1 | 10/2001 | Fodor et al. |
| 6,310,041 B1 | 10/2001 | Haddox et al. |
| 6,319,504 B1 | 11/2001 | Gallo et al. |
| 6,329,573 B1 | 12/2001 | Lightfoot et al. |
| 6,361,992 B1 | 3/2002 | Szkudlinski et al. |
| 6,379,970 B1 | 4/2002 | Liebler et al. |
| 6,416,959 B1 | 7/2002 | Giuliano et al. |
| 6,489,296 B1 | 12/2002 | Grinnell et al. |
| 6,507,788 B1 | 1/2003 | Camara y Ferrer et al. |
| 6,518,021 B1 | 2/2003 | Thastrup et al. |
| 6,539,102 B1 | 3/2003 | Anderson et al. |
| 6,583,109 B1 | 6/2003 | Gallo et al. |
| 6,586,403 B1 | 7/2003 | Mathison et al. |
| 6,596,688 B1 | 7/2003 | Gallo et al. |
| 6,620,416 B1 | 9/2003 | Gallo et al. |
| 6,630,138 B2 | 10/2003 | Gerlitz et al. |
| 6,642,201 B1 | 11/2003 | Khavinson et al. |
| 6,645,934 B1 | 11/2003 | Rodemann et al. |
| 6,652,860 B1 | 11/2003 | Singh et al. |
| 6,699,656 B2 | 3/2004 | Gallo et al. |
| 6,711,563 B1 | 3/2004 | Koskas |
| 6,727,227 B1 | 4/2004 | Khavinson |
| 6,783,757 B2 | 8/2004 | Brudnak |
| 6,831,057 B2 | 12/2004 | Baldwin et al. |
| 6,844,315 B2 | 1/2005 | Khan et al. |
| 6,852,697 B1 | 2/2005 | Mathison et al. |
| 6,894,028 B2 | 5/2005 | Lipton et al. |
| 6,921,751 B1 | 7/2005 | Khan et al. |
| 7,094,760 B2 | 8/2006 | Mathison et al. |
| 7,135,286 B2 | 11/2006 | Margus et al. |
| 7,175,679 B2 * | 2/2007 | Khan et al. ............ 514/2 |
| 7,316,819 B2 | 1/2008 | Grotts et al. |
| 7,358,330 B2 | 4/2008 | Khan et al. |
| 7,365,155 B2 | 4/2008 | Khan et al. |
| 7,368,535 B2 | 5/2008 | Ouspenski |
| 7,402,322 B2 | 7/2008 | Khan et al. |
| 7,501,391 B2 | 3/2009 | Khan et al. |
| 7,517,529 B2 | 4/2009 | Khan et al. |
| 7,560,433 B2 | 7/2009 | Khan et al. |
| 2002/0041871 A1 | 4/2002 | Brudnak |
| 2002/0064501 A1 | 5/2002 | Khan et al. |
| 2002/0147306 A1 | 10/2002 | Lin et al. |
| 2002/0183255 A1 | 12/2002 | Lipton et al. |
| 2003/0017203 A1 | 1/2003 | Crotts et al. |
| 2003/0049273 A1 | 3/2003 | Gallo et al. |
| 2003/0113733 A1 | 6/2003 | Khan et al. |
| 2003/0119720 A1 | 6/2003 | Khan et al. |
| 2003/0166556 A1 | 9/2003 | Khan et al. |
| 2003/0186244 A1 | 10/2003 | Margus et al. |
| 2003/0215434 A1 | 11/2003 | Khan et al. |
| 2003/0219425 A1 | 11/2003 | Khan et al. |
| 2003/0220257 A1 | 11/2003 | Benner et al. |
| 2003/0220258 A1 | 11/2003 | Benner et al. |
| 2003/0220259 A1 | 11/2003 | Benner et al. |
| 2003/0220260 A1 | 11/2003 | Khan et al. |
| 2003/0220261 A1 | 11/2003 | Khan et al. |
| 2003/0224995 A1 | 12/2003 | Khan et al. |
| 2004/0013661 A1 | 1/2004 | Wensvoort et al. |
| 2004/0208885 A1 | 10/2004 | Khan et al. |
| 2005/0037430 A1 | 2/2005 | Khan et al. |
| 2005/0107314 A1 | 5/2005 | Gorczynski et al. |
| 2005/0214943 A1 | 9/2005 | Khan et al. |
| 2005/0227925 A1 | 10/2005 | Benner et al. |
| 2006/0111292 A1 | 5/2006 | Khan et al. |
| 2006/0142205 A1 | 6/2006 | Benner et al. |
| 2006/0173162 A1 | 8/2006 | Djurup et al. |
| 2006/0275255 A1 | 12/2006 | Gudkov |
| 2007/0111948 A1 | 5/2007 | Turdiev |
| 2007/0197447 A1 | 8/2007 | Khan et al. |
| 2008/0076714 A1 | 3/2008 | Khan et al. |
| 2008/0171094 A1 | 7/2008 | Benner et al. |
| 2008/0176243 A1 | 7/2008 | Khan et al. |
| 2008/0194489 A1 | 8/2008 | Khan et al. |
| 2008/0242618 A1 | 10/2008 | Khan et al. |
| 2008/0242837 A1 | 10/2008 | Khan et al. |

FOREIGN PATENT DOCUMENTS

| | | |
|---|---|---|
| DE | 19953339 | 5/2001 |
| EP | 0 572 688 | 5/1997 |
| EP | 1 138 692 A1 | 10/2001 |
| EP | 1 300 418 | 4/2003 |
| EP | 1 224 212 B1 | 7/2003 |
| EP | 1 466 612 A1 | 10/2004 |
| FR | 2 706 772 | 12/1994 |
| GB | 2 194 886 A | 3/1988 |
| JP | 09-176187 A | 7/1997 |
| WO | WO 9220795 A1 | 11/1992 |
| WO | WO 96/04008 | 2/1996 |
| WO | WO 96/33218 | 10/1996 |
| WO | WO 97/49373 | 12/1997 |
| WO | WO 97/49418 | 12/1997 |
| WO | WO 97/49432 | 12/1997 |
| WO | WO 97/49721 | 12/1997 |
| WO | WO 98/06742 | 2/1998 |
| WO | WO 98/34631 A1 | 8/1998 |
| WO | WO 98/35691 | 8/1998 |
| WO | WO 99/31227 | 6/1999 |
| WO | WO 99/59617 | 11/1999 |
| WO | WO 00/17348 | 3/2000 |
| WO | WO 01/10907 A2 | 2/2001 |
| WO | WO 01/11048 A2 | 2/2001 |
| WO | WO 0110457 A2 | 2/2001 |
| WO | WO 01/29067 | 4/2001 |
| WO | WO 01/29069 A1 | 4/2001 |
| WO | WO 01/32196 A1 | 5/2001 |
| WO | WO 01/36454 A1 | 5/2001 |
| WO | WO 01/51508 A1 | 7/2001 |
| WO | WO 01/68113 A1 | 9/2001 |
| WO | WO 01/72831 | 10/2001 |
| WO | WO 01/83554 A2 | 11/2001 |
| WO | WO 02/085117 | 10/2002 |
| WO | WO 03/029292 A2 | 4/2003 |
| WO | WO 2006/069198 A1 | 6/2006 |

OTHER PUBLICATIONS

Connelly et al., "Biphasic Regulation of NF-kB Activity Underlies the Pro- and Anti-inflammatory Actions of Nitric Oxide," The Journal of Immunology, 2001, pp. 3873-3881, 166, The American Association of Immunologists, USA.

Friedlander, "Tackling anthrax," Nature, Nov. 8, 2001, pp. 160-161, vol. 414.

Ivanov et al., "Hemoglobin as a Source of Endogenous Bioactive Peptides: The Concept of Tissue-Specific Peptide Pool," Biopolymers, 1997, pp. 171-188, vol. 39.

Jyonouchi et al., "Proinflammatory and regulatory cytokine production associated with innate and adaptive immune responses in children with autism spectrum disorders and developmental regression," J Neuroim., 2001, pp. 170-179, vol. 120.

Kachra et al., "Low Molecular Weight Components but Not Dimeric HCG Inhibit Growth and Down-Regulate AP-1 Transcription Factor in Kaposi's Sarcoma Cells," Endocrinology, 1997, pp. 4038-4041, vol. 138, No. 9.

Kanungo et al., "Advanced Maturation of Heteropneustes Fossilis (Bloch) by Oral Administration of Human Chorionic Gonadotropin," J. Adv. Zool., 1999, pp. 1-5, vol. 20.

Keller et al., "Human Chorionic Gonadotropin (hCG) Is a Potent Angiogenic Factor for Uterine Endothelial Cells in Vitro," Placenta, Jul. 1999, pp. A37, vol.

Khan et al., "Inhibition of Diabetes in NOD Mice by Human Pregnancy Factor," Human Immunology, Dec. 2001, pp. 1315-1323, vol. 62, No. 12.

Khan et al., "Inhibition of Septic Shock in Mice by an Oligopeptide From the β-Chain of Human Chorionic Gonadotrophin Hormone," Human Immunology, Jan. 2002, pp. 1-7, vol. 63, No. 1.

Khavinson et al, Gerontological Aspects of Genome Peptide Regulation, 2005, S. Karger AG, Basel, Switzerland.

Khavinson et al., "Effects of Livagen Peptide on Chromatin Activation in Lymphocytes from Old People," Bulletin of Experimental Biology and Medicine, Oct. 2002, pp. 389-392, vol. 134, No. 4.

Khavinson et al., "Effects of Short Peptides on Lymphocyte Chromatin in Senile Subjects," Bulletin of Experimental Biology and Medicine, Jan. 2004, pp. 78-81, vol. 137, No. 1.

Khavinson et al., "Epithalon Peptide Induces Telomerase Activity and Telomere Elongation in Human Somatic Cells," Bulletin of Experimental Biology and Medicine, Jun. 2003, pp. 590-592, vol. 135, No. 6.

Khavinson et al., "Inductive Activity of Retinal Peptides," Bulletin of Experimental Biology and Medicine, Nov. 2002, pp. 482-484, vol. 134, No. 5.

Khavinson et al., "Mechanisms Underlying Geroprotective Effects of Peptides," Bulletin of Experimental Biology and Medicine, Jan. 2002, pp. 1-5. vol. 133, No. 1.

Khavinson et al., "Peptide Promotes Overcoming of the Division Limit in Human Somatic Cell," Bulletin of Experimental Biology and Medicine, May 2004, pp. 503-506, vol. 137, No. 5.

Lang et al., "Induction of apoplosis in Kaposi's sarcoma spindle cell cultures by the subunits of human chorionic gonadtropin," AIDS, 1997, pp. 1333-1340, vol. 11, No. 11.

Lunardi-Iskandar et al., "Effects of a urinary factor from women in early pregnancy on HIV-a, SIV and associated disease," Nature Medicine, Apr. 1998, pp. 428-434, vol. 4, No. 4.

Medzhitov, "Toll-like Receptors and Innate Immunity," Nature Reviews/Immunology, Nov. 2001, pp. 135-145, vol. 1.

Morozov et al., "Natural and Synthetic Thymic Peptides as Therapeutics for Immune Dysfunction," Int. J. Immunopharmac., 1997, pp. 501-505, vol. 19, No. 9/10.

Muchmore et al., "Immunoregulatory Properties of Fractions from Human Pregnancy Urine: Evidence that Human Chorionic Gonadotropin is not Responsible," The Journal of Immunology, Mar. 1997, pp. 881-886, vol. 118, No. 3.

Muchmore et al., "Purification and Characterization of a Mannose-Containing Disaccharide Obtained from Human Pregnancy Urine," Journal of Experimental Medicine, Dec. 1984, pp. 1672-1685, vol. 160.

Patil et al., "The Study of the Effect of Human Chorionic Gonadotrophic (HCG) Hormone on the Survival of Adrenal Medulla Transplant in Brain. Preliminary Study," ACTA Neurochir (WIEN), 1987, pp. 76-78, vol. 87.

Rohrig et al., "Growth-stimulating Influence of Human Chorionic Gonadotropin (hCG) on Plasmodium falciparum in vitro," Zeniralblail Baki, 1999, pp. 89-99, vol. 289.

Samaniego et al., "Induction of Programmed Cell Death in Kaposi's Sarcoma Cells by Preparations of Human Chorionic Gonadotropin," Journal of the National Cancer Institute, Jan. 20, 1999, pp. 135-143, vol. 91, No. 2.

Slater et al., "Decreased Mortality of Murine Grail-Versus-Host Disease by Human Chorionic gonadotropin," Transplantation, Jan. 1977, pp. 103-104, vol. 23, No. 1.

Tak et al., "NF-kappaB: a key role in inflammatory diseases," J Clin Invest., 2001, pp. 7-11, vol. 107.

Tan et al., "The role of activation of nuclear factor-kappa B of rat brain in the pathogenesis of experimental allergic encephalomyelitis," Acta Physiol Sinica, 2003, pp. 58-64, vol. 55.

Tovey et al., "Mucosal Cytokine Therapy: Marked Antiviral and Antitumor Activity," J. Interferon Cytokine Res., 1999, pp. 911-921, vol. 19.

Wulczyn et al., "The NF-kB/Rcl and IkB gene families: mediators of immune response and inflammation," J. Mol. Med., 1996, pp. 749-769, vol. 74, No. 12.

Yamamoto et al., "Role of the NF-kB Pathway in the Pathogenesis of Human Disease States," Current Molecular Medicine, Jul. 2001, pp. 287-296, vol. 1, No. 3.

Abeyama et al., A role of NF-κB-dependent gene transactivation in sunburn. The Journal of Clinical Investigation, vol. 105, No. 12, pp. 1751-1759, Jun. 2000.

Abraham, E., "Coagulation Abnormalities in Acute Lung Injury and Sepsis," Am. J. Respir. Cell Mol. Biol., 2000, pp. 401-404, vol. 22.

Adib-Conquy et al., "NF-κB Expression in Mononuclear Cells in Patients with Sepsis Resembles That Observed in Lipopolysaccharide Tolerance," Am. J. Respir. Crit. Care Med., 2000, pp. 1877-1883, vol. 162.

Agawal et al., Acute Renal Failure, American Family Physician, 2000, pp. 2077-2088, vol. 61, corresponding to web version of p. 1-20.

Arima et al., "IL-2-Induced Growth of CD8+ T Cell Prolymphocytic Leukemia Cells Mediated by NF-kappaB Induction and IL-2 Receptor alpha Expression," Leukemia Research, 1998, pp. 265-273, vol. 22, No. 3.

Baeuerle et al., "Function and Activation of NF-κB in the Immune System," Annu. Rev. Immunol., 1994, pp. 141-179, vol. 12.

Bethea et al., "Traumatic Spinal Cord Injury Induces Nuclear Factor-κB Activation," The Journal of Neuroscience, May 1, 1998, pp. 3251-3260, vol. 18, No. 9.

Bodfish et al., "Treating the Core Features of Autism: Are We There Yet?" Mental Retardation and Developmental Disabilities Research Reviews, 2004, pp. 318-326, vol. 10.

Bradham et al., Activation of nuclear factor- κB during orthotopic liver transplantation in rats is protective and does not require Kuppfer cells, Liver Transplantation and Surgery, Jul. 1999, pp. 282-293, vol. 5, No. 4.

Brown et al., "Two Forms of NF-κB1 (p105/p50) in Murine Macrophages: Differential Regulation by Lipopolysaccharide, Interleukin-2, and Interferon-gamma," Journal of Interferon and Cytokine Research, 1997, pp. 295-306, vol. 17.

Cook et al., Modified total lymphoid irradiation and low dose coricosteroids in progressive multiple sclerosis, Journal of Neurological Sciences, vol. 152, pp. 172-181, 1997.

Cui et al., Am. J. Physiol. Integr. Comp. Physiol., 2004. pp. R699-R709, vol. 286.

Dwinnell et al., Atlas of Diseases of the Kidney, Blackwell Sciences, 1999, pp. 12.1-12.12, Ch. 12.

Emmel et al., "Cyclosporin A Specifically Inhibits Function of Nuclear Proteins Involved in T Cell Activation," Science, Dec. 22, 1989, pp. 1617-1620, vol. 246.

Epinat et al., "Diverse agents act at multiple levels to inhibit the Rel/NF-κB signal transduction pathway," Oncogene, 1999, pp. 6896-6909, vol. 18.

Faust et al., "Disseminated intravascular coagulation and purpura fulminans secondary to infection," Bailliere's Clinical Haematology, 2000, 179-197, vol. 13. No. 2.

Flores et al., NFκB and AP-1 DNA binding activity in patients with multiple sclerosis. J. Neuroimmunol. vol. 135, No. 1-2, pp. 141-147, Feb. 2003.

Jimenez-Garza et al., "Early Effects of Modulating Nuclear factor-κB Activation on Traumatic Spinal Cord Injury in Rats," Ann. N.Y Acad. Sci., 2005, pp. 148-150. vol. 1053.

Kalns et al., Biochem. Biophys. Res. Comm., 2002, pp. 506-509, vol. 297.

Kalns et al., Biochem. Biophys. Res. Comm., 2002, pp. 41-44, vol. 292.

Kidd et al., "Autism, An Extreme Challenge to Integrative Medicine. Part II: Medical Management," Alternative Medicine Review, 2002, pp. 472-499, vol. 7, No. 6.

Kronfol et al., "Cytokines and the Brain: Implications for Clinical Psychiatry," Am. J. Psychiatry, May 2000., pp. 683-694, vol. 157, No. 5.

Li et al., "NF-κB Regulation in the Immune System," Nature Reviews/Immunology, Oct. 2002, pp. 725-734, vol. 2.

Malek-Ahmadi, P., "Role of Cytokines in Psychopathology: Therapeutic Implications," Drug News Prospects, Jun. 1998, pp. 271-276, vol. 11, No. 5.

McBean et al., "Rodent Models of Global Cerebral Ischemia: A Comparison of Two-Vessel Occlusion and Four-Vessel Occlusion," Gen. Pharmac., 1998, pp. 431-434, vol. 30, No. 4.

McDonald et al., "Interleukin-15 (IL-15) Induces NF-κB Activation and IL-8 Production in Human Neutrophils," Blood, Dec. 15, 1998, pp. 4828-4835, vol. 92, No. 12.

MedlinePlus, Medical Encyclopedia: autoimmune disorders (www.nlm.giv/medlineplus/ency/article/000816.htm).

Merck Index, 17th ed. 1999, pp. 1145-1146, 1841-1848, 2539, 2551.

Merriam-Webster Medical Dictionary, 1994, p. 82.

Moayeri et al., Journal of Clinical Investigation, Sep. 2003, pp. 670-682, vol. 112, No. 5.

Neely et al., "Then and now: Studies using a burned mouse model reflect trends in burn research over the past 25 years," Burns, 1999, pp. 603-609, vol. 25.

Ngo et al., The protein folding problem and tertiary structure prediction, 1994, pp. 492-494.

Oka et al., Immunosuppression in organ transplantation, Japanese Journal of Pharmacology, vol. 71, No. 2, pp. 89-100, Jun. 1996.

Pellizzari et al., FEBS Letters, 1999, pp. 199-204, vol. 462.

Smith et al., "Recent developments in drug therapy for multiple sclerosis," Multiple Sclerosis, 1999, pp. 110-120. vol. 5.

Traystman, R., "Animal Models of Focal and Global Cerebral Ischemia," ILAR Journal, 2003, pp. 85-95, vol. 44, No. 2.

Weinberger et al., "Mechanisms Mediating the Biologic Activity of Synthetic Proline, Glycine, and Hydroxyproline Polypeptides in Human Neutrophils," Mediators of Inflammation, 2005, pp. 31-38, vol. 1.

Yang et al., "Increased cortical nuclear factor κB (NF-κB) DNA binding activity after traumatic brain injury in rats," Neuroscience Letters, 1995, pp. 101-104, vol. 197.

Zhou et al., Transplantation tolerance in NF-κB-impaired mice is not due to regulation but is prevented by transgenic expression of Bcl-xL. The Journal of Immunology, vol. 174, No. 6, pp. 3447-3453, Mar. 2005.

PCT International Search Report, PCT/NL/2006/000329 dated Jan. 18, 2007.

Barton et al., Protective Role of Interleukin 6 in the Lipopolysaccharide-Galactosamine Septic Shock Model, Infection and Immunity, Apr. 1993, pp. 1496-1499, vol. 61, No. 4.

Burdelya et al., NF-kappaB activating proteins as radioprotectants: Derivatives of Flagellin from Salmonella protect mice from hematopoietic and gastrointestinal Radiation Syndromes, Cleveland Biolabs, Inc.

Burdelya et al., An agonist of toll-like receptor 5 has radioprotective activity in mouse and primate models, Abstract, Science, Apr. 11, 2008, pp. 226-230, vol. 320, No. 5873.

Clerici et al., Single-cell analysis of cytokine production shows different immune profiles in multiple sclerosis patients with active or quiescent disease. Journal of Neuroimmunology, vol. 121, pp. 33-101, 2001.

Cleveland BioLabs, Inc., Radiation Antidote for Defense, (visited Apr. 16, 2008) <http://www.cbiolabs.com/Applications.php.

Corvino et al., Availability, stability and sterility of pralidoxime for mass casualty use, Abstract, Ann Emerg Med., Mar. 2006, pp. 272-277, vol. 47, No. 3.

Daemen et al., Ischemia-reperfusion-induced IFN-gamma up-regulation: involvement of IL-12 and IL-13, The Journal of Immunology, 1999, pp. 5506-5510, vol. 162.

De Saizieu et al., Journal of Bacteriology, vol. 182, No. 17, pp. 4696-4703, Sep. 2000.

Dechend et al., Oncogene, vol. 18, pp. 3316-3323, 1999.

Dietrich et al., Postischemic hypothermia and IL-10 treatment provide long-lasting neuroprotection fo CA1 hippocampus following transient global ischemia in rats. Experimental Neurology, 1999, pp. 444-450, vol. 158.

Donnahoo et al., Early kidney TNF-alpha expression mediates neutrophil infiltration and injury after renal ischemia-reperfusion, American Journal of Physiology, Sep. 1999, pp. R922-R929, vol. 277, No. 3, Pt. 2.

Eckardt et al., Hypoxia-induced accumulation of erythropoietin mRNA in isolated hepatocytes is inhibited by protein kinase C, Pflugers Archiv., 1994, pp. 21-30, vol. 426.

GenBank Accession No. NP_000728, GI: 4502789, publicly available Apr. 2007.

Garkavtsev et al., Suppression of the novel growth inhibitor p33INGI promotes neoplastic transformation, Nature Publishing Group, Dec. 14, 1996, pp. 415-420.

Garkavtsev et al., The candidate tumour suppressor p33INGI cooperates with p53 in cell growth control, Nature, Jan. 15, 1998, pp. 295-298, vol. 391.

Gudkov, Andrei V., Cancer drug discovery: the wisdom of imprecision, Nature Medicine, Dec. 2004, 1298-00, vol. 10, No. 12.

Gudkov et al., The role of p53 in determining sensitivity to radiotherapy, Nature Reviews, Feb. 2003, pp. 117-129, vol. 3.

Gudkov, Andrei V., Converting p53 from a killer into a healer, Nature Medicine, Nov. 2002, pp. 1196-1198, vol. 8, No. 11.

Han et al., Cholecystokinin induction of mob-1 chemokine expression in pancreatic acinar cells requires NF-kappaB activation, American Journal of Physiology, Jul. 1999, vol. 277, pp. C74-C82.

Huang et al., Ischemia-reperfusion and immediate T cell responses, Cellular Immunology, 2007, pp. 4-11, vol. 248.

Husek et al., Rapid screening of urinary proline-hydroxyproline dipeptide in bone turnover studies, Abstract, J. Chromatogr B Analyt Technol Biomed Life Sci., Feb. 5, 2002, pp. 169-174, vol. 767, No. 1.

Ichiyama et al., Systemically administered alpha-melanocyte-stimulating peptides inhibit NF-kappaB activation in experimental brain inflammation, Brain Research, Jul. 1999, pp. 31-37, vol. 836.

Iyer et al., The transcriptional program in the response of human fibroblasts to serum, Science, Jan. 1999, pp. 83-87, vol. 283, No. 5398.

Keeton and Gould, Biological Science, 5th Ed., New York, W.W. Norton & Company, Inc. 1993, p. 4.

Lane et al., Interleukin-10 reduces the systemic inflammatory response in a murine model of intestinal ischemia/reperfusion, Surgery, 1997, pp. 288-294, vol. 122, No. 2.

Le Moine et al., Cold liver ischemia-reperfusion injury critically depends on liver T cells and is improved by donor pretreatment with interleukin 10 in mice, Hepatology, 2000, pp. 1266-1274, vol. 31, No. 6.

Lin et al., The Journal of Biological Chemistry, vol. 270, No. 24, pp. 14255-14258, Jun. 1995.

Lutterova et al., Marked difference in tumor necrosis factor-alpha expression in warm ischemia- and cold ischemia-reperfusion of the rat liver, Cryobiology, 2000, pp. 301-314, vol. 41.

Malyak et al., Characterization of a Low Molecular Weight Isoform of IL-1 Receptor Antagonist, The Journal of Immunology, 1998, pp. 1997-2003, vol. 161.

Ohlsson et al., Interleukin-1 Receptor Antagonist Reduces Mortality from Endotoxin Shock, Nature, Dec. 6, 1990, pp. 550-552, vol. 348.

Olszyna et al., Levels of Inhibitors of Tumor Necrosis Factor Alpha and Interleukin 1b in Urine and Sera of Patients with Urosepsis, Infection and Immunity, Aug. 1998, pp. 3527-3534.

Pan et al., Bradykinin Stimulates NF-κB Activation and Interleukin 1β Gene Expression in Cultured Human Fibroblasts, J. Clin. Invest., Nov. 1996, pp. 2042-2049, vol. 93, No. 9, The American Society for Clinical Investigation, Inc.

Partial European Search Report for 02 763 111.8 dated Nov. 23, 2007.

PCT International Search Report, International Application No. PCT/NL02/00639, mailed Aug. 4, 2003.

PCT International Search Report, PCT/EP2005/003707, dated Jul. 5, 2005.

PCT International Search Report, PCT/NL01/00259, dated Dec. 18, 2001.

PCT International Search Report and Written Opinion, PCT/NL2007/050092, dated Jul. 6, 2007.

Qin et al., Nuclear Factor kB Nuclear Translocation Upregulates c-Myc and p53 Expression during NMDA Receptor-Mediated Apoptosis in Rat Striatum, The Journal of Neuroscience, May 15, 1999, pp. 4023-4033, vol. 19, No. 10.

Quillan et al., Combinatorial diffusion assay used to identify topically active melanocyte-stimulating hormone receptor antagonists, PNAS, Mar. 1995, pp. 2894-2898, vol. 92, USA.

"RDT&E Budget item justification sheet" StartDateMarker 1999, EndDateMarker Retrieved from the Internet: URL:http://www.dtic.mil/descriptivesum/Y2000/OSD/PE0602787D.pdf>.

Riera et al., Neutrophils accentuate renal cold ischemia-reperfusion injury. Dose-dependent protective effect of platelet-activating factor receptor antagonist, The Journal of Pharmacology and Experimental Therapeutics, 1997, pp. 786-794, vol. 280, No. 2.

Rodriguez et al., Expression of human HLA-B27 transgene alters susceptibility to murine theiler's virus-induced demylenination, 1991, vol. 146, pp. 2596-2602.

Selzman et al., Interleukin-10 inhibits postinjury tumor necrosis factor-mediated human vascular smooth muscle proliferation, Journal of Surgical Research, 1998, pp. 352-356, vol. 80.

Sharma, Septic Shock, (visited Sep. 27, 2007 <http://www.emedicine.com/MED/topic2101.htm>.

Sovak et al., Aberrant nuclear factor-kappa B/Rel expression and the pathogenesis of breast cancer, The Journal of Clinical Investigation, Dec. 1997, pp. 2952-2960, vol. 100, No. 12.

Strom et al., Small-molecule inhibitor of p53 binding to mitochondria protects mice from gamma radiation, Nature Chemical Biology, Sep. 2006, pp. 474-479, vol. 2, No. 9.

Szinicz, L., History of chemical and biological warfare agents, Abstract, Toxicology, Oct. 30, 2005, pp. 167-181, vol. 214, No. 3.

Thibonnier et al., Cytoplasmic and nuclear signaling pathways of VI-vascular vasopressin receptors, Regulatory Peptides, 1993, pp. 79-84, vol. 45.

Valore et al., Human b-Defensin-1: An antimicrobial Peptide of Urogenital Tissues, J. Clin. Invest., Apr. 1998, pp. 1633-1642, vol. 101, No. 8.

Wallraff et al., Urinary Excretion of Amino Acids in Pregnancy, J. Clinc. Invest., 1950, pp. 1542-1544, vol. 29.

Wu et al., Gonadotropin-Releasing Hormone (GNRH) Cleavage Products are Involved in the Regulation of GNRH Gene Expression in the GTI-7 Neuronal Cell Line, Society for Neuroscience Abstracts, Nov. 4, 2000, pp. 7.8, XP009091566, vol. 26, No. 1-2.

Baud et al., Signaling by proinflammatory cytokines: oligomerization of TRAF2 and TRAF6 is sufficient for JNK and IKK activation and target gene induction via an amino-terminal effector domain, Genes & Development, May 1999, pp. 1297-1308, vol. 13.

Borchardt, RT, Optimizing oral absorption of peptides using prodrug strategies, Journal of Controlled Release, Nov. 1999, pp. 231-238, vol. 62.

Engles et al., Exogenous human recombinant interleukin-10 attenuates hindlimb ischemia-repferusion injury, Journal of Surgical Research, 1997, pp. 425-428, vol. 69.

Fassio et al., Transforming Growth Factor Alpha and Its Receptor in Neural Retina, Investigative Ophthalmology & Visual Science, Sep. 1989, pp. 1916-1922, vol. 30, No. 9.

Manna et al., Human chorionic gonadotropin suppresses activation of nuclear transcription factor-kappa B and activator protein-1 induced by tumor necrosis factor, The Journal of Biological Chemistry, May 2000, pp. 13307-13314, vol. 275, No. 18.

Padmos et al., A discriminating messenger RNA signature for bipolar disorder formed by an aberrant expression of inflammatory genes in monocytes, Arch Gen Psychiatry, Apr. 2008, pp. 395-407, vol. 65, No. 4.

PCT International Search Report. PCT/CA97/00568, dated Apr. 30, 1998.

Redon et al., Global variation in copy number in the human genome, Nature, Nov. 23, 2006, pp. 444-454, vol. 444.

Bastin et al., Salt Selection and Optimisation Procedures for Pharmaceutical new Chemical Entities. Org. Proc. Res. Develop. 2000, pp. 427-435, vol. 4.

Gould, Salt selection for basic drugs, Int. J. Pharm., 1986, pp. 201-217. vol. 33.

http://www.rxlist.com/cgi/generic/chorionic.htm—RX List.com entry for hCG/Pregnyl.

Kato et al., Reduced hepatic ischemia/reperfusion injury by IL-4: potential anti-inflammatory role of STAT6, Inflammation Research, Jun. 2000, pp. 275-279, vol. 49, No. 6.

NCBI Accession No. AA106724, version Oct. 6, 2006.

Office Action for U.S. Appl. No. 10/409,032 dated Jun. 1, 2009.

Office Action for U.S. Appl. No. 11/037,972 dated Dec. 12, 2008.

Notice of Allowance for U.S. Appl. No. 11/346,450 dated Apr. 7, 2009.

Office Action for U.S. Appl. No. 11/481,423 dated Apr. 16, 2009.

Office Action for U.S. Appl. No. 11/593,329 dated Apr. 6, 2009.

Office Action for U.S. Appl. No. 11/600,294 dated Apr. 3, 2009.

Office Action for U.S. Appl. No. 11/715,314 dated Feb. 26, 2009.

Office Action for U.S. Appl. No. 11/975,284 dated Dec. 29, 2008.

Office Action for U.S. Appl. No. 11/982,170 dated Nov. 19, 2008.

Office Action for U.S. Appl. No. 11/982,292 dated May 18, 2009.

U.S. Appl. No. 12/383,849, filed Mar. 27, 2009, Khan et al., Compositions for Mucosal and Oral Administration comprising HCG Fragments.

U.S. Appl. No. 12/386,061, filed Apr. 9, 2009, Khan et al., Methods and Uses for Protein Breakdown Products.

U.S. Appl. No. 12/386,135, filed Apr. 14, 2009, Khan et al., Gene Regulator.

* cited by examiner

US 7,662,776 B2

TREATMENT OF TUMORS USING SHORT PEPTIDES FROM HUMAN CHORIONIC GONADOTROPIN (HCG)

CROSS-REFERENCE TO RELATED APPLICATION

This application claims the benefit, under 35 U.S.C. §119 (e) to provisional patent application U.S. Ser. No. 60/696,657, filed on Jul. 5, 2005, the contents of the entirety of which is incorporated by this reference.

TECHNICAL FIELD

The invention relates generally to biotechnology, and more specifically to methods of affecting tumor growth using peptides, such as tri-mers, 4-mers, 5-mers, 6-mers, 7-mers, and methods or treating subjects with a peptide and pharmaceutical compositions containing a peptide.

BACKGROUND

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer subjects who initially survive their primary cancers, common experience has shown that their lives are dramatically altered. Many cancer subjects experience strong anxieties driven by the awareness of the potential for recurrence or treatment failure. Many cancer subjects also experience physical debilitations during or following treatment. Furthermore, many cancer subjects experience a recurrence.

Due to the recurrence rates and side effects of current cancer treatments, improved cancer treatments represent a great need in society. Preferably, those treatments are small molecules that are easily adsorbed by the body, cheap and easy to manufacture, effective, and do not have many of the side effect associated with current cancer treatments.

DISCLOSURE OF THE INVENTION

Where it was generally thought that the smallest breakdown products of proteins have no specific biological function on their own, it now emerges that the body may utilize the normal process of proteolytic breakdown to generate important compounds. In particular, certain short breakdown products of hCG (i.e., short peptides, derivates, or functional analogues which can easily be synthesized and used in a pharmaceutical composition) can be used to limit the progression of tumors.

The current invention relates to understanding and/or predicting the body's innate way of responding to small molecules and builds on insights reported in PCT International Publications WO 099/59617, WO 01/72831, and WO03/29292, the contents of the entirety of all of which are incorporated herein by this reference. These applications describe small gene-regulatory peptides that are present in pregnant women that are derived from proteolytic breakdown of placental gonadotropins, such as hCG. These breakdown products are often only about three to six amino acids long and were shown to have unsurpassed immunological activity that is exerted by regulating expression of genes encoding inflammatory mediators such as cytokines. Surprisingly, it was found that breakdown of hCG provides a cascade of peptides that helps maintain a pregnant woman's immunological homeostasis. These peptides balance the immune system to assure that the mother stays immunologically sound while her fetus does not get prematurely rejected during pregnancy, but instead is safely carried until its time of birth. Other peptides known in the art have the antigenic binding activity of human chorionic gonadotropin (hCG). See, e.g., U.S. Pat. No. 5,380,668 to Herron (Jan. 10, 1995), the contents of the entirety of which are incorporated by this reference. The oligopeptides disclosed therein are disclosed generally for use in diagnostic methods.

Other patents and patent applications, relate to the use of short polypeptides to modulate biological systems. For example the patents an applications to Gallo et al. (e.g., U.S. Pat. No. 5,677,275 (corresponding to WO 96/04008 A1), U.S. Pat. No. 5,877,148 (also corresponding to WO 96/04008 A1), WO 97/49721 A1, U.S. Pat. No. 6,319,504 (corresponding to WO 97/49373), U.S. Patent Application No. 2003/0049273 A 1 (also corresponding to WO 97/49373), U.S. Pat. No. 5,968,513 (corresponding to WO 97/49418), U.S. Pat. No. 5,997,871 (corresponding to WO 97/49432), U.S. Pat. No. 6,620,416, U.S. Pat. No. 6,596,688, WO 01/11048 A2, WO 01/10907 A2., and U.S. Pat. No. 6,583,109),disclose various oligopeptides and their use in, among other things, "inhibiting HIV infection," "treating or preventing HIV infection," "treating or preventing cancer," "treating or preventing a condition characterized by loss of body cell mass," "treating or preventing a condition associated with pathological angiogenesis," "treating or preventing hematopoietic deficiency," "ex vivo gene therapy," "expanding blood cells in vitro," and/or "providing blood cells to a subject."

In an exemplary embodiment, the present invention provides a method for identifying one or more peptides; and/or determining the activity of one or more peptides, comprising, for instance, screening a peptide to determine the activity of the peptide; analyzing the results; and/or identifying one or more peptide having anti-tumor activity.

In a further embodiment, derivates or functional analogues of anti-tumor peptides may be created.

The invention provides methods for reducting tumor growth by administering a pharmaceutical composition comprising a pharmacologically effective amount of at least one anti-tumor peptide or a derivative or a functional analogue thereof together with a pharmaceutically acceptable diluent to the subject. A particular useful pharmaceutically acceptable diluent is sterile water or an isotonic salt solution such as 0.9% saline or phosphate buffered salt (PBS). In a preferred embodiment, the invention provides the treatment of a subject suffering or believed to be suffering from cancer by mucosal, preferably oral administration of a pharmaceutical composition comprising a pharmacologically effective amount of two or more anti-tumor peptides, derivatives, or functional analogues thereof together with a pharmaceutically acceptable diluent to the subject.

The invention thus provides use of an anti-tumor peptide pharmaceutical composition for application to a subject for reducing tumor size and/or inhibiting tumor progression. Useful examples of such an anti-tumor peptides can be selected from the group of oligopeptides LQG, LAG, LQGV (SEQ ID NO:1), AQGV (SEQ ID NO:2), LAGV (SEQ ID NO:3), VLPALP (SEQ ID NO:4), and functional analogues or derivatives thereof. Functional analogues can, for example, be found in urinary fractions derived from pregnant woman or in commercial preparations of hCG; at least in those commercial preparations that contain substantial amounts of breakdown products of hCG.

A preferred size of an anti-tumor peptide for inclusion in a pharmaceutical composition according to the invention is at most 15 amino acids, preferably at most seven amino acids, although much smaller molecules of 3, 4, 5, or 6 amino acids in length are particularly effective.

The invention also provides use of a peptide of smaller than 30 amino acids for the production of a pharmaceutical composition for the treatment a subject suffering from or believed to be suffering from cancer. It is preferred that said peptide be smaller than 15 amino acids. When peptides are used repeatedly, for example, as is provided herein for the treatment of cancer, from a safety viewpoint it is preferred that said peptide is smaller than seven amino acids, such a peptide generally not binding to the MHC receptors, thereby decreasing the risk of the development of autoimmunity initiated by an immune response against administered peptide.

Subjects suffering from cancer will already benefit from the anti-inflammatory properties of some of the small peptides identified herein, but surprisingly most benefit will come from the anti-cell cycle activity of the small peptides, notably of the 3- and 4-mer peptides at dosages of above 1 mg/kg, preferably of above 5 mg/kg, more preferably of above 10 mg/kg body weight. Considering the low immunogenic nature of the small peptides (i.e., those of three to four aa), dosing to up to 100 mg/kg with small peptides, and in some cases when need for treatment is determined to be acute considering the condition of the subject in need of treatment, of up to 200 mg/kg, 500 mg/kg or even 1 g/kg will be possible.

Furthermore, it is particularly useful that subjects in need of treatment for cancer can now be treated via a subcutaneous or intra-muscular injection, thereby allowing self-treatment with an autoinjector or treatment by non-trained or non-medical personnel.

Other peptides, especially 3- or 4-mer peptides, can be found by testing for anti-cell cycle activity in proliferation assays, for example, by using a plant growth assay as provided herein. Use of a peptide for the production of a pharmaceutical composition for the treatment a subject suffering from or believed to be suffering from cancer wherein said peptide consists of two to six amino acids is herein particularly provided. From the viewpoint of preventing adverse reactions, such as anaphylactic shock, it is thus preferred that the pharmaceutical composition comprises a peptide that consists of two to six amino acids, more preferably consists of three to five amino acids, and most preferably consists of three or four amino acids. If only from the viewpoint of activity, based on a general insight that activity is broader with increasing peptide size, if only to withstand full proteolysis (after administration) longer whereby metabolic fragments of three aa still have activity, it is herein preferred that said peptide consists of four amino acids.

Several useful 3-mer peptides for use in the production of a pharmaceutical composition for treatment of cancer are identified herein as VVC, LAG, and AQG. The invention also provides use of peptide VVC, LAG, or AQG for the production of a pharmaceutical composition for the treatment of cancer, preferably for the treatment of metastatic carcinoma. Treatment according to the invention with a 3-mer peptide preferably comprises repeated administration, preferably three times weekly or every second day, with a dose of at least 5 mg peptide/kg bodyweight of a patient, more preferably with a dose of at least 17 mg peptide/kg bodyweight, more preferably with a dose of at least 50 mg peptide/kg bodyweight peptide.

Similarly, several useful 4-mer peptides for treatment of cancer are LQGV (SEQ ID NO:1), QVVC (SEQ ID NO:5), MTRV (SEQ ID NO:6), AQGV (SEQ ID NO:2), LAGV (SEQ ID NO:3), LQAV (SEQ ID NO:7), PGCP (SEQ ID NO:8), VGQL (SEQ ID NO:9), RVLQ (SEQ ID NO:10), EMFQ (SEQ ID NO:11), AVAL (SEQ ID NO:12), FVLS (SEQ ID NO:13), NMWD (SEQ ID NO:14), LCFL (SEQ ID NO:15), FSYA (SEQ ID NO:16), FWVD (SEQ ID NO:17), AFTV (SEQ ID NO:18), LGTL (SEQ ID NO:19), QLLG (SEQ ID NO:20), YAIT (SEQ ID NO:21), APSL (SEQ ID NO:22), ITTL (SEQ ID NO:23), QALG (SEQ ID NO:24), GVLC (SEQ ID NO:25), NLIN (SEQ ID NO:26), SPIE (SEQ ID NO:27), LNTI (SEQ ID NO:28), LHNL (SEQ ID NO:29), CPVQ (SEQ ID NO:30), EVVR (SEQ ID NO:31), MTEV (SEQ ID NO:32), EALE (SEQ ID NO:33), EPPE (SEQ ID NO:34), LGTL (SEQ ID NO:19), VGGI (SEQ ID NO:35), RLPG (SEQ ID NO:36), LQGA (SEQ ID NO:37), and LCFL (SEQ ID NO:15), useful 5-mer peptides for treatment of cancer are TLAVE (SEQ ID NO:38), VEGNL (SEQ ID NO:39), and LNEAL (SEQ ID NO:40), useful 6-mer peptides for treatment of cancer are VLPALP (SEQ ID NO:4), MGGTWA (SEQ ID NO:41), LTCDDP (SEQ ID NO:42), useful 7-mer peptides for treatment of cancer are VLPALPQ (SEQ ID NO:43), VCNYRDV (SEQ ID NO:44), and CPRGVNP (SEQ ID NO:45), a useful 8-mer peptide for treatment of cancer is QPLAPLVG (SEQ ID NO:46) and a useful 9-mer peptide for treatment of cancer is DINGFLPAL (SEQ ID NO:47).

The invention also provides use of LQGV (SEQ ID NO:1), QVVC (SEQ ID NO:5), MTRV (SEQ ID NO:6), AQGV (SEQ ID NO:2), LAGV (SEQ ID NO:3), LQAV (SEQ ID NO:7), PGCP (SEQ ID NO:8), VGQL (SEQ ID NO:9), RVLQ (SEQ ID NO:10), EMFQ (SEQ ID NO:11), AVAL (SEQ ID NO:12), FVLS (SEQ ID NO:13), NMWD (SEQ ID NO:14), LCFL (SEQ ID NO:15), FSYA (SEQ ID NO:16), FWVD (SEQ ID NO:17), AFTV (SEQ ID NO:18), LGTL (SEQ ID NO:19), QLLG (SEQ ID NO:20), YAIT (SEQ ID NO:21), APSL (SEQ ID NO:22), ITTL (SEQ ID NO:23), QALG (SEQ ID NO:24), GVLC (SEQ ID NO:25), NLIN (SEQ ID NO:26), SPIE (SEQ ID NO:27), LNTI (SEQ ID NO:28), LHNL (SEQ ID NO:29), CPVQ (SEQ ID NO:30), EVVR (SEQ ID NO:31), MTEV (SEQ ID NO:32), EALE (SEQ ID NO:33), EPPE (SEQ ID NO:34), LGTL (SEQ ID NO:19), VGGI (SEQ ID NO:35), RLPG (SEQ ID NO:36), LQGA (SEQ ID NO:37), or LCFL (SEQ ID NO:15) for the production of a pharmaceutical composition for the treatment of cancer, preferably for the treatment of metastatic carcinoma. Treatment according to the invention with a 4-mer peptide preferably comprises repeated administration, preferably three weekly or every second day, with a dose of at least 5 mg peptide/kg bodyweight of a patient, more preferably with a dose of at least 17 mg peptide/kg bodyweight, more preferably with a dose of at least 50 mg peptide/kg bodyweight peptide.

The invention also provides use of TLAVE (SEQ ID NO:38), VEGNL (SEQ ID NO:39), or LNEAL (SEQ ID NO:40) for the production of a pharmaceutical composition for the treatment of cancer, preferably for the treatment of metastatic carcinoma. Treatment according to the invention with a 5-mer peptide preferably comprises repeated administration, preferably three weekly or every second day, with a dose of at least 5 mg peptide/kg bodyweight of a patient, more preferably with a dose of at least 17 mg peptide/kg bodyweight, more preferably with a dose of at least 50 mg peptide/kg bodyweight peptide.

The invention also provides use of VLPALP (SEQ ID NO:4), MGGTWA (SEQ ID NO:41), or LTCDDP (SEQ ID NO:42) for the production of a pharmaceutical composition for the treatment of cancer, preferably for the treatment of metastatic carcinoma. Treatment according to the invention with a 6-mer peptide preferably comprises repeated administration, preferably three weekly or every second day, with a dose of at least 5 mg peptide/kg bodyweight of a patient, more preferably with a dose of at least 17 mg peptide/kg bodyweight, more preferably with a dose of at least 50 mg peptide/kg bodyweight peptide.

This size of smaller than seven amino acids (aa) is also particularly preferred because it was determined (when comparing peptides derived from the human proteome with those derived from pathogen proteomes, in particular of viruses or bacteria (Burroughs et al., *Immunogenetics,* 2004, 56:311-320)) that with a peptide size of seven aa only 3% overlap between self or non-self is found. For peptides of six aa, that overlap in human self with pathogen non-self was determined to be 30%, for peptides of five aa, 90%, and for four aa long (and smaller) peptides, 100% overlap between the peptides present in the human proteome and the peptides present in the proteome of pathogens was determined. Based on these data, it is now herein recognized that when the self-non-self difference is not present, risk of adverse immune reactions, such as anaphylactic shock, is greatly diminished, which is a distinct advantage when treatment against cancer with a peptide according to the invention comprises repeat administration, such as repeated injections or three weekly injections for a prolonged period of, for example, three weeks as provided herein.

From the viewpoint of preventing adverse reactions such as anaphylactic shock it is thus preferred that the peptide consists of two to six amino acids, more preferably consists of three to five amino acids, and most preferably consists of three or four amino acids. From the viewpoint of activity, based on a general insight that activity is broader with increasing peptide size, if only to withstand full proteolysis longer whereby metabolic fragments of three aa still have activity, it is herein preferred that said peptide consists of four amino acids. Above and below described compositions are preferably used for the treatment of cancer.

Very suitable peptides for use in the treatment of cancer according to the invention are VVC, LAG, AQG, LQGV (SEQ ID NO:1), QVVC (SEQ ID NO:5), MTRV (SEQ ID NO:6), AQGV (SEQ ID NO:2), LAGV (SEQ ID NO:3), LQAV (SEQ ID NO:7), PGCP (SEQ ID NO:8), VGQL (SEQ ID NO:9), RVLQ (SEQ ID NO:10), EMFQ (SEQ ID NO:11), AVAL (SEQ ID NO:12), FVLS (SEQ ID NO:13), NMWD (SEQ ID NO:14), LCFL (SEQ ID NO:15), FSYA (SEQ ID NO:16), FWVD (SEQ ID NO:17), AFTV (SEQ ID NO:18), LGTL (SEQ ID NO:19), QLLG (SEQ ID NO:20), YAIT (SEQ ID NO:21), APSL (SEQ ID NO:22), ITTL (SEQ ID NO:23), QALG (SEQ ID NO:24), GVLC (SEQ ID NO:25), NLIN (SEQ ID NO:26), SPIE (SEQ ID NO:27), LNTI (SEQ ID NO:28), LHNL (SEQ ID NO:29), CPVQ (SEQ ID NO:30), EVVR (SEQ ID NO:31), MTEV (SEQ ID NO:32), EALE (SEQ ID NO:33), EPPE (SEQ ID NO:34), LGTL (SEQ ID NO:19), VGGI (SEQ ID NO:35), RLPG (SEQ ID NO:36), LQGA (SEQ ID NO:37), LCFL (SEQ ID NO:15), TLAVE (SEQ ID NO:38), VEGNL (SEQ ID NO:39), or LNEAL (SEQ ID NO:40). Herewith, the invention also provides a pharmaceutical composition having anti-cell cycle activity useful in the treatment of cancer. The cell cycle is an ordered set of events, culminating in cell growth and division into two daughter cells. The stages of the cell cycle are G1-S-G2-M. The G1 stage stands for "GAP 1." The S stage stands for "Synthesis." This is the stage when DNA replication occurs. The G2 stage stands for "GAP 2." The M stage stands for "mitosis," and is when nuclear (chromosomes separate) and cytoplasmic (cytokinesis) division occur. The term "anti-cell cycle activity" as used herein is meant to indicate that the peptide is capable of altering cell cycle dynamics. For example, it comprises altering, i.e., increasing or reducing, the frequency of cell division. In one embodiment, it refers to an anti-proliferative activity.

Provided is a pharmaceutical composition having anti-cell cycle activity useful in the treatment of cancer comprising PGCP (SEQ ID NO:8), a pharmaceutical composition having anti-cell cycle activity useful in the treatment of cancer comprising VGQL (SEQ ID NO:9), a pharmaceutical composition having anti-cell cycle activity useful in the treatment of cancer comprising RVLQ (SEQ ID NO:10), a pharmaceutical composition having anti-cell cycle activity useful in the treatment of cancer comprising EMFQ (SEQ ID NO:11), a pharmaceutical composition having anti-cell cycle activity useful in the treatment of cancer comprising AVAL (SEQ ID NO:12), a pharmaceutical composition having anti-cell cycle activity useful in the treatment of cancer comprising FVLS (SEQ ID NO:13), a pharmaceutical composition having anti-cell cycle activity useful in the treatment of cancer comprising NMWD (SEQ ID NO:14), a pharmaceutical composition having anti-cell cycle activity useful in the treatment of cancer comprising LCFL (SEQ ID NO: 15), a pharmaceutical composition having anti-cell cycle activity useful in the treatment of cancer comprising FSYA (SEQ ID NO: 16), a pharmaceutical composition having anti-cell cycle activity useful in the treatment of cancer comprising FWVD (SEQ ID NO: 17), a pharmaceutical composition having anti-cell cycle activity useful in the treatment of cancer comprising AFTV (SEQ ID NO:18), a pharmaceutical composition having anti-cell cycle activity useful in the treatment of cancer comprising LGTL (SEQ ID NO:19), a pharmaceutical composition having anti-cell cycle activity useful in the treatment of cancer comprising QLLG (SEQ ID NO:20), a pharmaceutical composition having anti-cell cycle activity useful in the treatment of cancer comprising YAIT (SEQ ID NO:21), a pharmaceutical composition having anti-cell cycle activity useful in the treatment of cancer comprising APSL (SEQ ID NO:22), a pharmaceutical composition having anti-cell cycle activity useful in the treatment of cancer comprising ITTL (SEQ ID NO:23), a pharmaceutical composition having anti-cell cycle activity useful in the treatment of cancer comprising QALG (SEQ ID NO:24), a pharmaceutical composition having anti-cell cycle activity useful in the treatment of cancer comprising GVLC (SEQ ID NO:25), a pharmaceutical composition having anti-cell cycle activity useful in the treatment of cancer comprising NLIN (SEQ ID NO:26), a pharmaceutical composition having anti-cell cycle activity useful in the treatment of cancer comprising SPIE (SEQ ID NO:27), a pharmaceutical composition having anti-cell cycle activity useful in the treatment of cancer comprising LNTI (SEQ ID NO:28), a pharmaceutical composition having anti-cell cycle activity useful in the treatment of cancer comprising LHNL (SEQ ID NO:29), a pharmaceutical composition having anti-cell cycle activity useful in the treatment of cancer comprising CPVQ (SEQ ID NO:30), a pharmaceutical composition having anti-cell cycle activity useful in the treatment of cancer comprising EVVR (SEQ ID NO:31), a pharmaceutical composition having anti-cell cycle activity useful in the treatment of cancer comprising MTEV (SEQ ID NO:32), a pharmaceutical composition having anti-cell cycle activity useful in the treatment of cancer comprising EALE (SEQ ID NO:33), a pharmaceutical composition having anti-cell cycle activity useful in the treatment of cancer comprising EPPE (SEQ ID NO:34), a pharmaceutical composition having anti-cell cycle activity useful in the treatment of cancer comprising LGTL (SEQ ID NO:19), a pharmaceutical composition having anti-cell cycle activity useful in the treatment of cancer comprising VGGI (SEQ ID NO:35), a pharmaceutical composition having anti-cell cycle activity useful in the treatment of cancer comprising RLPG (SEQ ID NO:36), a pharmaceutical composition having anti-cell cycle activity useful in the treatment of cancer comprising LQGA (SEQ ID NO:37), a pharmaceutical composition having anti-cell cycle activity useful in the treatment of cancer comprising LCFL (SEQ ID NO:15), a pharmaceutical composition having anti-cell cycle activity useful in the treatment of cancer comprising TLAVE (SEQ ID NO:38), a pharmaceutical composition having anti-cell cycle activity useful in the treatment of cancer comprising VEGNL (SEQ ID NO:39), a pharmaceutical composition having anti-cell cycle activity useful in the treatment of cancer comprising LNEAL (SEQ ID NO:40), a pharmaceutical composition having anti-cell cycle activity useful in the treatment of cancer comprising MGGTWA (SEQ ID NO:41), a pharmaceutical composition having anti-cell cycle activity useful in the treatment of cancer comprising LTCDDP (SEQ ID NO:42), a pharmaceutical composition having anti-cell cycle activity useful in the treatment of cancer comprising VCNYRDV (SEQ ID NO:44), a pharmaceutical composition having anti-cell cycle activity useful in the treatment of cancer comprising CPRGVNP (SEQ ID NO:45), and a pharmaceutical composition having anti-cell cycle activity useful in the treatment of cancer comprising DINGFLPAL (SEQ ID NO:47).

DETAILED DESCRIPTION OF THE INVENTION

Figure 1:
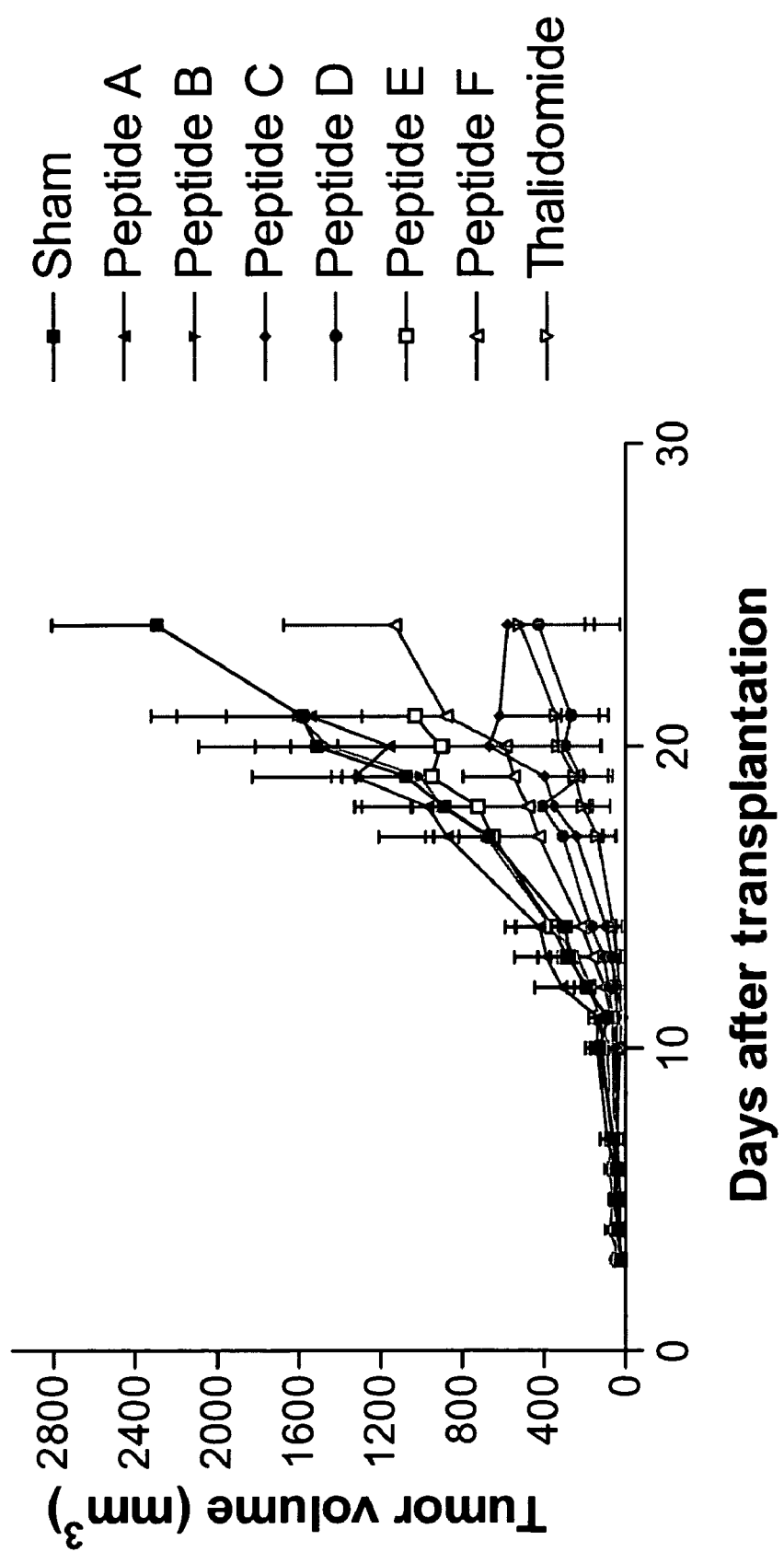
FIG. 1 illustrates tumor volumes of mice treated with exemplary peptides of the invention wherein Peptides A through F correspond to the peptides LAG, LAGV (SEQ ID NO:3), LQG, LQGV (SEQ ID NO:1), AQGV (SEQ ID NO:2), and VLPALP (SEQ ID NO:4), respectively.

As used herein, a "purified or isolated" peptide is one that has been purified from a natural or biotechnological source, or, more preferably, is synthesized as described herein.

"Treating" or "treatment" does not require a complete cure. It means that the symptoms of the underlying disease are at least reduced, and/or that one or more of the underlying cellular, physiological, or biochemical causes or mechanisms causing the symptoms are reduced and/or eliminated. It is understood that reduced, as used in this context, means relative to the state of the disease, including the molecular state of the disease, not just the physiological state of the disease.

"Composition," as used herein, refers to chemical compounds which contain or consist of a peptide or a derivative or functional analogue thereof. The peptide is preferably isolated before inclusion within the composition. The peptide preferably consists of three (3) to six (6) amino acids and most preferredly consists of three (3) or four (4) amino acids.

As used herein, a "functional analogue" or "derivative" of a peptide includes variations made with regard to a reference peptide, which retains an identifiable relationship to the reference peptide, including variations made by pepscan, ala-scanning, replacement net analysis, methods disclosed in U.S. patent application Ser. No. 10/456,375, as well as non-conservative and/or conservative substitutions relative to a reference sequence, for example, MTRVLQGVL-PALPQVVC (SEQ ID NO:48). Derivatives also include compounds having the same or equivalent sidechains as the particular amino acids used in a peptide, and arranged sequentially in the same order as the peptides, but joined together by non-peptide bonds, for instance, by isosteric linkages such as the keto isostere, hydroxy isostere, diketo isostere, or the keto-difluoromethylene isostere. Once a derivative is produced, such a derivative is a peptide for the purposes of screening, identification of activity, inclusion in a database, production of a pharmaceutical and the like.

Also included within derivatives or functional analogues are peptidomimetic compounds that functionally or structurally resemble the original peptide taken as the starting point, but that are, for example, composed of non-naturally occurring amino acids or polyamides. With "conservative amino acid substitution," one amino acid residue is substituted with another residue with generally similar properties (size, hydrophobicity, and/or charge), such that the overall functioning of a peptide sequence having such substitution is likely not to be seriously affected. In "non-conservative amino acid substitution," one amino acid residue is substituted with another residue with generally different properties (size, hydrophobicity, and/or charge), such that the overall functioning of a peptide sequence having such substitution is could be seriously affected. A derivative can also be provided by systematically altering at least one amino acid of the reference peptide. This can, for instance, be done by an Alanine scanning (Ala-scan) and/or replacement net analysis, in which each amino acid is replaced in turn with one of the 19 (or 21, if selenocysteine and pyrrolysine are included) other amino acids. With these methods, many different peptides may be generated, based on an original amino acid sequence but each containing a variation or substitution of at least one amino acid residue. This way, many positional variants of the original amino acid sequence are synthesized and/or enzymatically prepared.

Peptidomimetics further include pseudopeptides having surrogates for the peptide bonds between the original amino acids. (See, e.g., U.S. Pat. No. 6,689,753 to Soto-Jara). Such surrogates for peptide bonds include, but are not limited to $CH_2$, $CH_2CH_2$, $CH=CH$, $C\equiv C$, $CH_2NH$, $COCH_2$, $CH_2S$, $CH_2SO_2$, and NHCO.

Further included within derivatives or functional analogues are peptides that have been chemically modified through, for example, glycosylation, PEGylation, PEG alkylation, alkylation, acteylation, amidation, glycosyl-phophatdylinositalization, farnesylation, ADP-ribosylation, sulfation, lipid attachment, hydroxylation, and phosphorylation.

A derivative or analogue can also be, for instance, generated by substitution of an L-amino acid residue with a D-amino acid residue or other non-natural residues. Such a substitution may improve a property of an amino acid sequence, for example, to provide a peptide sequence of known activity of all D-amino acids in retro inversion format, thereby allowing for retained activity and increased half-life values. By generating many positional variants (derivatives) of an original amino acid sequence and screening for a specific activity, an improved peptide, for example, comprising D-amino acids, can be identified and used according to the invention.

Furthermore, a compound could, in one embodiment be:

NT Xaa$_1$ Xaa$_2$ Xaa$_3$ Xaa$_4$ CT wherein NT at the N-terminus is selected from the group of H—, CH3-, an acyl group, or a general protective group; and CT at the C-terminus is selected from the group of small (for instance, one to five amino acids) peptides, —OH, —OR$^1$, —NH$_2$, —NHR$^1$, —NR$^1$ R$^2$, or —N(CH$_2$)$_{1-6}$ NR$^1$ R$^2$, wherein R$^1$ and R$^2$, when present, are independently selected from H, alkyl, aryl, (ar)alkyl, and wherein R$^1$ and R$^2$ can be cyclically bonded to one another. Such modifications constitute derivatives of the reference peptide.

"Alkyl" as used herein, is preferably a saturated branched or unbranched hydrocarbon having one to six carbon atoms, for instance, methyl, ethyl, and isopentyl.

"Aryl" as used herein, is an aromatic hydrocarbon group, preferably having six to ten carbon atoms, such as phenyl or naphthyl.

"(Ar)alkyl," as used herein, is an arene group (having both aliphatic and aromatic portions), preferably having from seven to thirteen carbon atoms such as benzyl, ethylbenzyl, n-propylbenzyl, and isobutylbenzyl.

"Peptide," as used herein, means peptides having from three to about fifty amino acids joined together by peptide bonds.

"Composition" also includes, for example, an acceptable salt of the oligopeptide or a labeled peptide. As used herein, "acceptable salt" refers to salts that retain the desired activity of the peptide or equivalent compound, but preferably do not detrimentally affect the activity of the peptide or other component of a system, which uses the peptide. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts may be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (for instance, a zinc tannate salt).

The composition can be administered or introduced in vivo systemically, topically, orally, or locally. The composition can be administered as a pharmaceutically acceptable acid- or base-addition salt, formed by reaction with an inorganic acid (such as hydrochloric acid, hydrobromic acid, perchloric acid, nitric acid, thiocyanic acid, sulfuric acid, and phosphoric acid); or with an organic acid (such as formic acid, acetic acid, propionic acid, glycolic acid, lactic acid, pyruvic acid, oxahc acid, malonic acid, succinic acid, maleic acid, and fumaric acid); or by reaction with an inorganic base (such as sodium hydroxide, ammonium hydroxide, potassium hydroxide); or with an organic base (such as mono- , di- , trialkyl and aryl amines and substituted ethanolamines). A peptide may also be conjugated to sugars, lipids, other peptides, nucleic acids and PNA; and function in situ as a conjugate or be released locally after reaching a targeted tissue or organ.

The compounds according to the invention may be prepared by methods known in the art (for example, see, U.S. patent application Ser. No. 10/456,375). For example, by peptide synthesis methods known in the art, including, suitable N alpha protection (and side-chain protection if reactive side-chains are present). The amino acid derivatives or peptides are activated and coupled to suitably carboxyl protected amino acid or peptide derivatives either in solution or on a solid support. Protection of the α-amino group may utilize an acid-labile tertiary-butyloxycarbonyl group ("Boc"), benzyloxycarbonyl ("Z") group or substituted analogs or the base-labile 9-fluoremyl-methyloxycarbonyl ("Fmoc") group. The Z group can also be removed by catalytic hydrogenation, other suitable protecting groups include Nps, Bmv, Bpoc, Aloc, MSC, etc. A good overview of amino protecting groups is given in *The peptides, Analysis, Synthesis, Biology*, Vol. 3 E. Gross and J. Meienhofer, eds. (Academic Press, New York, 1981). Protection of carboxyl groups can take place by ester formation, for example, base-labile esters like methyl or ethyl, acid labile esters like tertiary butyl or, substituted, benzyl esters or hydrogenolytically. Protection of side-chain functions like those of lysine and glutamic or aspartic acid can take place using the aforementioned groups. Protection of thiol, and although not always required, of guanidino, alcohol and imidazole groups can take place using a variety of reagents such as those described in *The Peptides, Analysis, Synthesis, Biology*, or in *Pure and Applied Chemistry*, 59(3), 331-344 (1987). Activation of the carboxyl group of the suitably protected amino acids or peptides can take place by the azide, mixed anhydride, active ester, or carbodiimide method especially with the addition of catalytic and racemization-suppressing compounds like 1-N—N-hydroxybenzotriazole, N-hydroxysuccin-imide, 3-hydroxy-4-oxo-3,4-dihydro-1,2, 3,-benzotriazine, N-hydroxy-5 norbornene-2,3-dicar-boxyimide. Also the anhydrides of phosphorus based acids can be used. See, e.g., *The Peptides, Analysis, Synthesis, Biology*, supra and *Pure and Applied Chemistry*, 59(3), 331-344 (1987).

It is also possible to prepare the compounds by the solid phase method of Merrifield. Different solid supports and different strategies are known see, e.g., Barany and Merrifield in *The Peptides, Analysis, Synthesis, Biology*, Vol. 2, E. Gross and J. Meienhofer, eds. (Acad. Press, New York, 1980), Kneib-Cordonier and Mullen *Int. J. Peptide Protein Res.*, 30, 705-739 (1987) and Fields and Noble *Int. J. Peptide Protein Res.*, 35, 161-214 (1990). The synthesis of compounds in which a peptide bond is replaced by an isostere, can, in general, be performed using the previously described protecting groups and activation procedures. Procedures to synthesize the modified isosteres are described in the literature for instance, for the —CH$_2$—NH— isostere and for the —CO—CH$_2$— isostere.

Removal of the protecting groups, and, in the case of solid phase peptide synthesis, the cleavage from the solid support may be performed by means known in the art (see, e.g., volumes 3, 5 and 9 of the series on *The Peptides Analysis, Synthesis, Biology*, supra).

Another possibility is the application of enzymes in synthesis of such compounds; for reviews see, e.g., H. D. Jakubke in *The Peptides, Analysis, Synthesis, Biology*, Vol. 9, S. Udenfriend and J. Meienhofer, eds. (Acad. Press, New York, 1987). For example, by modifications such as glycosylation, phosphorylation and other modifications known in the art.

Peptides according to the invention may also be made according to recombinant DNA methods. Such methods involve the preparation of the desired peptide by means of expressing recombinant polynucleotide sequence which codes for one or more of the oligopeptides in a suitable host cell. Generally, the process involves introducing into a cloning vehicle (for instance, a plasmid, phage DNA, or other DNA sequence able to replicate in a host cell) a DNA sequence coding for the particular oligopeptide or oligopeptides, introducing the cloning vehicle into a suitable eucaryotic or procaryotic host cell, and culturing the host cell thus transformed. When a eucaryotic host cell is used, the compound may include a glycoprotein portion.

Pharmaceutical compositions containing the peptides described herein are administered to a subject suffering from or believed to be suffering from cancer. In therapeutic applications, compositions are administered to a subject in an amount sufficient to cause regression of the tumor, or at least partially arrest the tumorgenesis and metastasis. An amount adequate to accomplish this is defined as a "therapeutically effective dose." Amounts effective for this use will depend on, for instance, the nature of the peptide (specific activity, etc.), the manner of administration, the stage and severity of the cancer, the weight and general state of health of the subject, and the judgment of the prescribing physician.

Single or multiple administrations of a peptide composition can be carried out with dose levels and pattern being selected by a treating physician. In any event, the pharmaceutical formulations should provide a quantity of peptide sufficient to effectively treat the subject. Administration should begin at the first indication of undesirable cellular proliferation or shortly after diagnosis, and continue until symptoms are substantially abated and for a period thereafter. In well established cases of cancer, loading doses followed by maintenance doses may be required.

The pharmaceutical compositions for therapeutic treatment are intended for parenteral, topical, oral or local administration. The invention provides compositions for parenteral administration which comprise a solution of an anti-tumor peptide dissolved or suspended in an acceptable carrier, preferably an aqueous carrier. A variety of aqueous carriers can be used, for instance, water, buffered water, 0.4% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Other methods for preparing pharmaceutical compositions will be known or apparent to those skilled in the art and are described in more detail in, for example, *Remington's Pharmaceutical Science*, 19th ed., Mack Publishing Company, Easton, Pa. (1990), which is incorporated herein by reference.

For solid compositions of the peptides of the invention, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more anti-tumor peptides, more preferably at a concentration of 25%-75%.

The present invention also includes a medicament that comprises at least one pharmaceutical agent contained within packaging material. The pharmaceutical agent is therapeutically effective for treating a tumor and may be selected from the group of peptides disclosed herein.

While most new drugs are intended to be administered orally, peptide based drugs may be subject to undesirable degradation, making alternative delivery methods, such as, intranasal administration or transdermal administration, more desirable, however, even with peptide based drugs, oral delivery is desirable (for instance, have good bioavailability).

As described in PCT International Publication No. WO 03/029292 A2 (published Apr. 10, 2003), PCT International Publication No. WO 01/72831 A2 (published Oct. 4, 2001), and U.S. Patent Application Publications 20020064501 A1 (published May 30, 2002), 20030119720 A1 (published Jun. 26, 2003), 20030113733 A1 (published Jun. 19, 2003), and 20030166556 A1 (published Sep. 4, 2003), the contents of all of which are incorporated by this reference, compositions containing purified or isolated oligopeptides described therein have immunoregulatory activity useful in, for example, the treatment of sepsis and other disease states and conditions. They also have gene regulatory activities.

The invention includes a method of screening compounds, including a purified or isolated peptide consisting of particular four to eight amino acid segments of the sequence MTRVLQGVLPALPQVVC (SEQ ID NO:48), and derivatives thereof. Anti-tumor activity may be determined by treating a mouse challenged with a tumor and monitoring the tumor over time. In one embodiment, the amino acid segment includes a tetrameric sequence (for instance, corresponding to the LQVG (SEQ ID NO:1)) portion of MTRVLQGVLPALPQVVC (SEQ ID NO:48), i.e., $Xaa_1$ $Xaa_2$ $Xaa_3$ $Xaa_4$, wherein $Xaa_1$ is a substituted or unsubstituted non-polar amino acid selected from the group consisting of Ala and Leu; $Xaa_2$ is a substituted or unsubstituted amino acid selected from the group consisting of Gln, Pro, and Ala; $Xaa_3$ is a substituted or unsubstituted Gly; and $Xaa_4$ is a substituted or unsubstituted non-polar amino acid selected from the group consisting of Val and Ala. For instance, the peptide could be selected from the group consisting of LQGV (SEQ ID NO:1), the derivative AQGV (SEQ ID NO:2), the derivative LQGA (SEQ ID NO:37), the derivative LAGV (SEQ ID NO:3), and the derivative LPGC (SEQ ID NO:61).

In another embodiment, the segment is six amino acids long, and comprises the sequence $$Xaa_1\ Xaa_2\ Pro\ Ala\ Xaa_2\ Xaa_3$$

wherein $Xaa_1$ is substituted or unsubstituted Val or Ala, wherein $Xaa_2$ is independently selected from substituted or unsubstituted Leu or Ala, and wherein $Xaa_3$ is a substituted or unsubstituted Pro or Ala.

In such an embodiment, the peptide can have a formula selected from the group consisting of VLPALP (SEQ ID NO:4), the derivative ALPALP (SEQ ID NO:51), the derivative VAPALP (SEQ ID NO:52), the derivative ALPALPQ (SEQ ID NO:53), the derivative VLPAAPQ (SEQ ID NO:54), the derivative VLPALAQ (SEQ ID NO:55), the derivative VLPALA (SEQ ID NO:56), VLPALPQ (SEQ ID NO:43), the derivative VLPALPA (SEQ ID NO:57), the derivative GVLPALP (SEQ ID NO:58), and the derivative VLAALP (SEQ ID NO:59).

In another embodiment, the composition has no more than eight amino acids, and includes an amino acid sequence consisting of:

$$Xaa_1\ Xaa_2\ Xaa_3\ Xaa_4$$

wherein $Xaa_1$ is a substituted or unsubstituted amino acid selected from the group of amino acids consisting of Ala, Leu, and Met, wherein $Xaa_2$ is a substituted or unsubstituted amino acid selected from the group of amino acids consisting of Gln, Thr, Ala, and Pro, wherein $Xaa_3$ is substituted or unsubstituted Gly or Arg, and wherein $Xaa_4$ is a substituted or unsubstituted amino acid selected from the group of amino acids consisting of Cys, Ala, and Val. Anti-tumor activity may be determined by treating a mouse challenged with a tumor and monitoring the tumor over time.

In such an embodiment, the sequence may be selected from the group consisting of Leu Gln Gly Val (SEQ ID NO:1), Ala Gln Gly Val (SEQ ID NO:2), Leu Gln Gly Ala (SEQ ID NO:37), Leu Ala Gly Val (SEQ ID NO:3), Leu Pro Gly Cys (SEQ ID NO:61), or Met Thr Arg Val (SEQ ID NO:6), or a derivative thereof.

In another embodiment, the segment may be the tetramer MTRV (SEQ ID NO:6) or QVVC (SEQ ID NO:5) or a derivative thereof.

The invention further includes a pharmaceutical composition comprising a purified or isolated peptide, or acid addition salt thereof, the purified or isolated peptide having anti-tumor activity.

The invention provides a method for the identification of a peptide useful in the treatment of a tumor comprising administering to a subject believed to be in need of such treatment a composition comprising a peptide, derivative or functional analogue thereof, the particular molecule capable of anti-tumor activity.

In another embodiment, the composition comprises at least two peptides or derivatives thereof. For example, each peptide being capable of anti-tumor activity. By way of example, the at least two oligopeptides may be selected from the group LQGV (SEQ ID NO:1), AQGV (SEQ ID NO:2), and VLPALP (SEQ ID NO:4) or peptides identified by a method described herein.

The invention also provides use of a composition according to the invention for the preparation of a pharmaceutical composition or medicament and methods of treating various medical conditions, such as an immune-mediated disorder.

The invention is further explained with the aid of the following illustrative examples.

EXAMPLES

Example I

Material and Methods

PEPTIDE SYNTHESIS: The peptides as mentioned herein such as LQG, AQG, LQGV (SEQ ID NO:1), AQGV (SEQ ID NO:2), LQGA (SEQ ID NO:37), VLPALP (SEQ ID NO:4), ALPALP (SEQ ID NO:51), VAPALP (SEQ ID NO:52), ALPALPQ (SEQ ID NO:53), VLPAAPQ (SEQ ID NO:54), VLPALAQ (SEQ ID NO:55), LAGV (SEQ ID NO:3), VLAALP (SEQ ID NO:59), VLPALA (SEQ ID NO:56), VLPALPQ (SEQ ID NO:43), VLAALPQ (SEQ ID NO:62), VLPALPA (SEQ ID NO:57), GVLPALP (SEQ ID NO:58), VVCNYRDVRFESIRLPGCPRGVNPV-VSYAVALSCQCAL (SEQ ID NO:63), RPRCRPINAT-LAVEKEGCPVCITVNTTICAGYCPT (SEQ ID NO:64), SKAPPPSLPSPSRLPGPS (SEQ ID NO:65), LQGVL-PALPQVVC (SEQ ID NO:66), SIRLPGCPRGVNPVVS (SEQ ID NO:67), LPGCPRGVNPVVS (SEQ ID NO:68), LPGC (SEQ ID NO:61), MTRV (SEQ ID NO:6), MTR, and VVC are prepared by solid-phase synthesis (R. B. Merrifield, *J. Am. Chem. Soc.*, 85:2149-2165 (1963)) using the fluorenylmethoxycarbonyl (Fmoc)/tert-butyl-based methodology (Atherton, 1985) with 2-chlorotrityl chloride resin (Barlos et al., *Int. J. Peptide Protein res.*, 37:513-520 (1991)) as the solid support.

The side-chain of glutamine is protected with a trityl function. The peptides are synthesized manually. Each coupling consisted of the following steps: (i) removal of the alpha-amino Fmoc-protection by piperidine in dimethylformamide (DMF), (ii) coupling of the Fmoc amino acid (3 eq) with diisopropylcarbodiimide (DIC)/1-hydroxybenzotriazole (HOBt) in DMF/N-methylformamide (NMP) and (iii) capping of the remaining amino functions with acetic anhydride/diisopropylethylamine (DIEA) in DMF/NMP. Upon completion of the synthesis, the peptide resin is treated with a mixture of trifluoroacetic acid (TFA)/$H_2O$/triisopropylsilane (TIS) 95:2.5:2.5. After 30 minutes, TIS was added until decolorization. The solution was evaporated in vacuo and the peptide precipitated with diethylether.

The crude peptides are dissolved in water (50-100 mg/ml) and purified by reverse-phase high-performance liquid chromatography (RP-HPLC). HPLC conditions are: column: Vydac TP21810C18 (10×250 mm); elution system: gradient system of 0.1% TFA in water v/v (A) and 0.1% TFA in acetonitrile (ACN) v/v (B); flow rate 6 ml/min; absorbance was detected from 190-370 nm. There were different gradient systems used. For example, for peptides LQG and LQGV (SEQ ID NO:1): ten minutes 100% A followed by linear gradient 0-10% B in fifty minutes. For example, for peptides VLPALP (SEQ ID NO:4) and VLPALPQ (SEQ ID NO:43): five minutes 5% B followed by linear gradient 1% B/minute. The collected fractions are concentrated to about 5 ml by rotation-film evaporation under reduced pressure at 40° C. The remaining TFA is exchanged against acetate by eluting two times over a column with anion exchange resin (Merck II) in acetate form. The eluate was concentrated and lyophilized in 28 hours. Peptides later were prepared for use by dissolving them in PBS.

Example II

Animals and tumor model: Mice (C57B16) are transplanted with the syngeneic Lewis Lung Carcinoma (LLC) subcutaneously.

Treatment modalities: mice are treated with small peptides or control substances beginning on the day of transplantation by i.p. injection. Mice are injected on Monday, Wednesday and Friday, until end of experiment. Experiment ends are based on: tumor size >20 mm, suffering of the animal, weight loss over 20%, ulcerations etc. Otherwise the experiment is terminated eight weeks after start.

Method of Efficacy Evaluation

Assessment of Tumor Response

Tumor diameter is measured in two directions by caliper measurements and tumor volume (V) is calculated using the formula V=0.4(A²×B) (where B represents the largest diameter and A the diameter perpendicular to B). The classification of tumor response is: progressive disease (PD), increase of tumor volume (>50%) within seven days (between day 3 and day 10 after begin of treatment); stable disease, tumor volume equal to volume at day 3 in a range of −25% and +25%; partial remission (R), tumor volume −25% to −90%, and complete response CR, (no) measurable tumor at 56 days after start of treatment.

Tumor growth evaluation is terminated when a tumor diameter of 20 mm is reached.

Assessment of Side-Effects

Side-effects are monitored on daily basis and classified according to protocol.

A) Weight of the animals is monitored daily.

B) Behavior of the animals.

C) Animals are checked for possible side effects such as diarrhea.

Results

Tumor Response

Mice were treated with i.p. injections of peptides 24 hours after implantation of LLC tumor. In all mice receiving PBS tumor developed which reached on average a tumor volume of 1600 mm³ in 21 days. Approximately tumor diameter was at that time point 16 mm. Thalidomide was used as a positive control. On day 21 an average tumor volume of 340 mm³ was observed, while 3/6 mice showed complete tumor control for 56 days.

Administration of peptides LQG, LQGV (SEQ ID NO:1), AQGV (SEQ ID NO:2), and VLPALP (SEQ ID NO:4) induced a tumor growth delay (with LQG and LQGV (SEQ ID NO:1) comparable to Thalidomide) (Table 1). Administration of peptide LQGV (SEQ ID NO:1) resulted in strong tumor growth delay.

TABLE 1

Tumor response in mice bearing LLC tumor during and after treatment with small peptides.

| group | Treatment | volume day 21 | tumor control | PD | NC | PR | CR |
|---|---|---|---|---|---|---|---|
| 1 | Sham | 1600 | 0/6 | 6 | | | |
| 2 | peptide LAG | 1550 | 2/6 | 4 | | 1 | 1 |
| 3 | peptide LAGV (SEQ ID NO:3) | 1600 | 2/6 | 3 | 1 | 1 | 1 |
| 4 | peptide LQG | 620 | 3/6 | | 4 | | 2 |
| 5 | peptide LQGV (SEQ ID NO:1) | 270 | 2/6 | 1 | 2 | 1 | 2 |
| 6 | peptide AQGV (SEQ ID NO:2) | 1030 | 2/6 | 3 | 1 | 2 | |
| 7 | peptide VLPALP (SEQ ID NO:4) | 880 | 3/6 | 1 | 2 | 1 | 2 |
| 8 | Thalidomide | 340 | 3/6 | | 3 | 1 | 2 |

In mice treated with Thalidomide, as well as peptide LQG, a tumor response meaning maximally a growth of 25% within seven days) was obtained in all animals. In animals treated with peptides LQGV (SEQ ID NO:1) and VLPALP (SEQ ID NO:4), five out of six mice showed a response. Due to the small animal numbers we found no significances concerning volume. However, response rate of animals treated with peptides LQG, LQGV (SEQ ID NO:1), and VLPALP (SEQ ID NO:4), as well as thalidomide (T), was significantly improved as compared to sham treated mice (LQG and T: p<0.002, LQGV (SEQ ID NO:1), and VLPALP (SEQ ID NO:4): p<0.015).

From these results it becomes clear that administration of peptides resulted in tumor growth delay or tumor control. As is shown in FIG. 1, comparable tumor growth curves were obtained when mice were treated with anti-tumor peptides LQG and LQGV (SEQ ID NO:1) or thalidomide.

Side Effects

Figure 2:
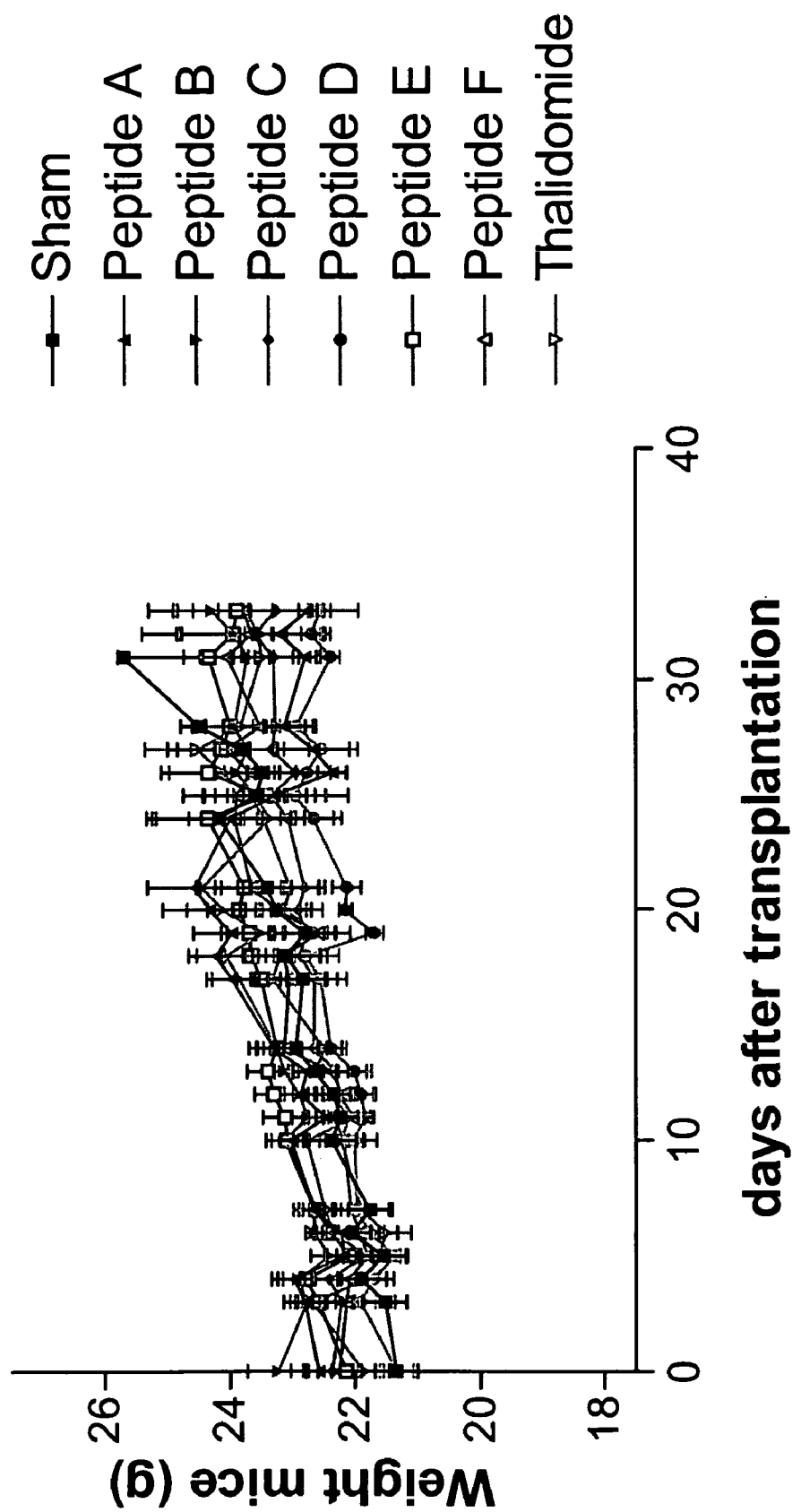
FIG. 2 illustrates the weight of tumor carrying mice treated with exemplary peptides of the invention wherein Peptides A through F correspond to the peptides LAG, LAGV (SEQ ID NO:3), LQG, LQGV (SEQ ID NO:1), AQGV (SEQ ID NO:2), and VLPALP (SEQ ID NO:4), respectively.
Figure 3:
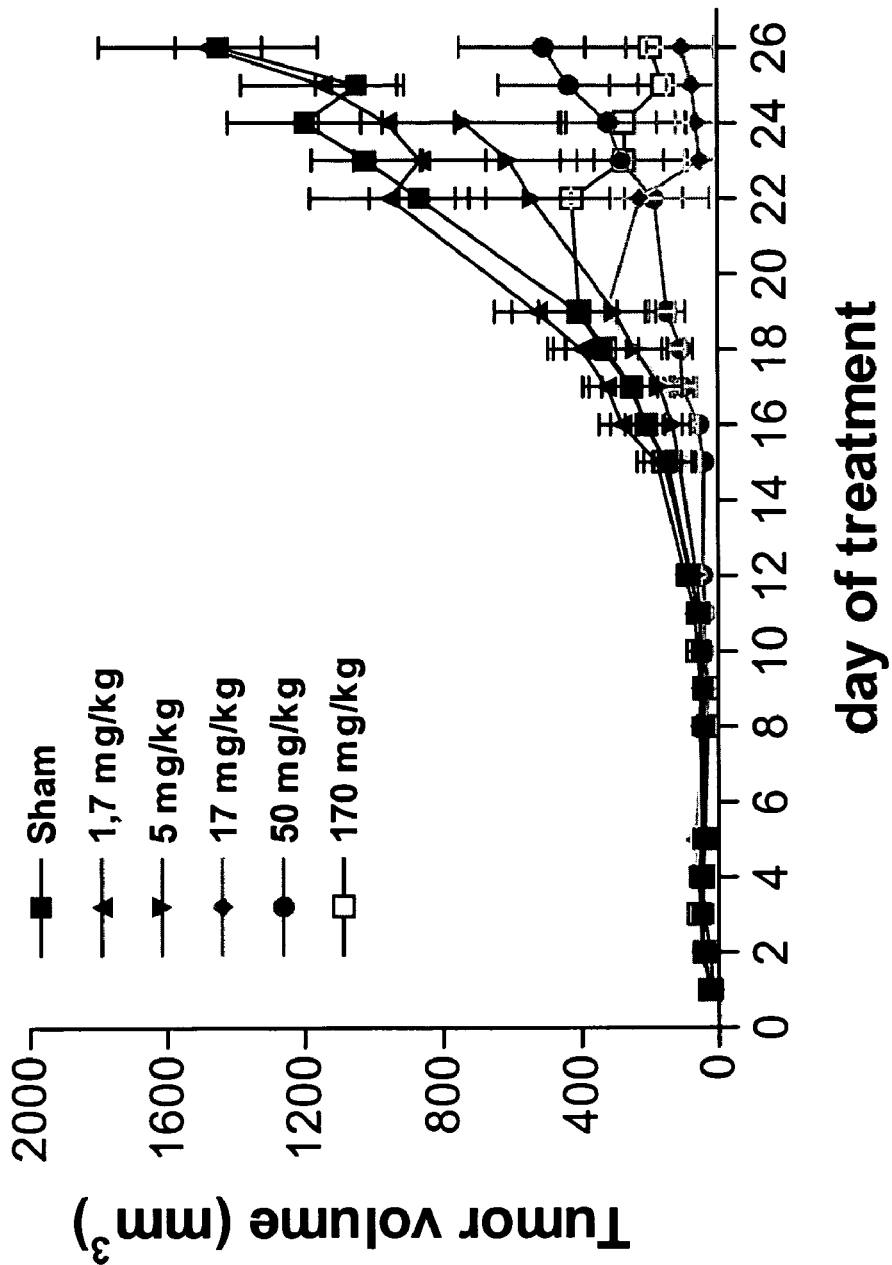
FIG. 3 Tumor volume of Lewis Lung Carcinoma-bearing C57B16 mice treated with escalating doses of peptide LQGV (SEQ ID NO:1). Doses of 1.7, 5, 17, 50 and 170 mg/kg were tested.

As shown in FIG. 2, no effect was observed on body weight in the mice treated with small peptides. Also no other side effects as mentioned were observed.

All references, including database accession numbers, publications, patents, and patent applications, cited herein are hereby incorporated by reference to the same extent as if each reference were individually and specifically indicated to be incorporated by reference and were set forth in its entirety herein.

Example III

Method of Testing

Animals and tumor model. Mice (C57B16) are transplanted with the syngeneic Lewis Lung Carcinoma (LLC) subcutaneously. Treatment is stared 24 hours after implantation. The number of animals is eight per group to increase the power of this study. As we are starting the treatment when no tumor is palpable the change of error is larger compared to a study with established tumors. Treatment modalities: mice are treated with small peptides or sham control beginning one day after transplantation by i.p. injection. Mice will be injected on Monday, Wednesday and Friday, until end of experiment. Experiment ends based on criteria as tumor size >20 mm, suffering of the animal, weight loss over 20%, ulcerations. Otherwise the experiment will be terminated eight weeks after start.

Method of Efficacy Evaluation

Assessment of Tumor Response

Tumor diameter is measured in two directions by caliper measurements and tumor volume (V) is calculated using the formula V=0.4(A2×B) (where B represents the largest diameter and A the diameter perpendicular to B). The classification of tumor response is: progressive disease (PD), increase of tumor volume (>25%) within seven days; no change (NC), tumor volume equal to volume at start of treatment in a range of −25% and +25%; partial remission (PR), decrease of tumor volume between −25% and −90%; complete remission (CR), tumor volume less than 10% of initial volume. Tumor growth evaluation is terminated when a tumor diameter of 20 mm is reached.

Assessment of side-effects. Side-effects are monitored on daily basis. a) Weight of the animals is monitored daily. b) Behavior of the animals is observed. c) Animals are checked for possible side effects such as diarrhea.

Statistics

Tumor volumes were analyzed using non-parametric testing for multiple groups (Kruskal Wallis) and pair wise comparison of the different groups using Mann Whitney.

Results

Figure 4:
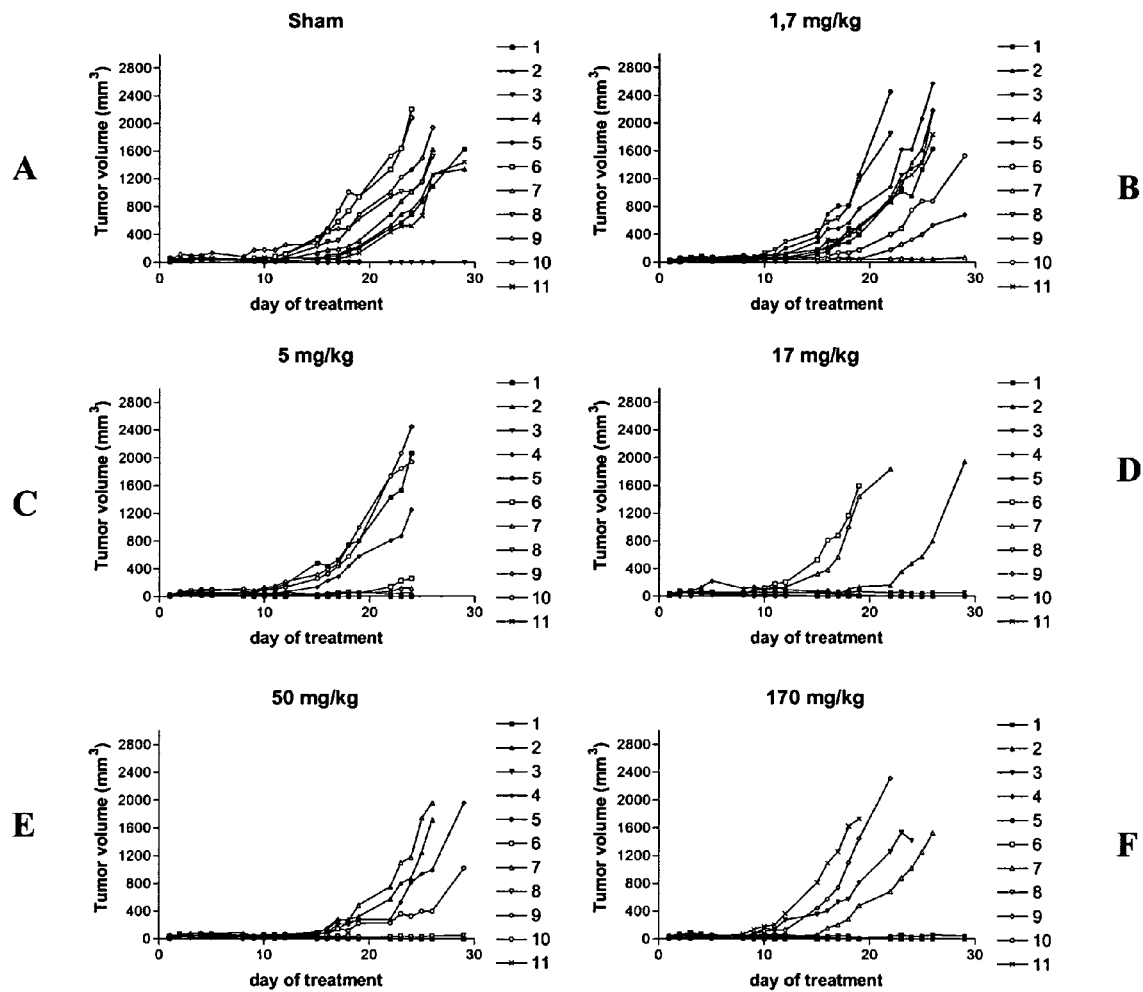
FIG. 4. Tumor growth curves of all individual mice treated with escalating doses of peptide LQGV (SEQ ID NO:1).

Mice were treated with escalating doses of peptide as described in Materials and Methods. At a dose of 5 mg/kg a delay in tumor growth was observed (FIG. 1). This delay was more pronounced in the higher dosages. Especially administration of 50 mg/kg strongly inhibited tumor growth. Control mice (negative: sham) demonstrated progressive tumor growth. Mice treated with Thalidomide (positive control) showed only some tumor growth delay. An overview of the individual tumor growth curves is presented in FIG. 4. Statistical analysis is depicted in Table 2.

TABLE 2

Statistical analysis of tumor volumes and tumor response in different peptide treatment groups. Tumor volumes at day 20 were compared. Upper right: tumor volumes. Lower left: tumor response (see Table 3).

|  | Sham | 1.7 mg/kg | 5 mg/kg | 17 mg/kg | 50 mg/kg | 170 mg/kg |
|---|---|---|---|---|---|---|
| Sham | — | 0.45 | 0.57 | 0.15 | 0.50 | 0.33 |
| 1.7 mg/kg | 0.62 | — | 0.70 | 0.01 | 0.002 | 0.06 |
| 5 mg/kg | 0.09 | 0.03 | — | 0.51 | 0.55 | 0.54 |
| 17 mg/kg | 0.01 | 0.004 | 0.35 | — | 0.63 | 0.94 |
| 50 mg/kg | 0.09 | 0.03 | 1.00 | 0.35 | — | 1.00 |
| 170 mg/kg | 0.09 | 0.03 | 1.00 | 0.35 | 1.00 | — |

TABLE 3

Tumor response rates

| Treatment | PD | TR | RR |
|---|---|---|---|
| Sham | 8 | 3 | 27% |
| 1.7 mg/kg | 9 | 2 | 18% |
| 5 mg/kg | 4 | 7 | 64% |
| 17 mg/kg | 2 | 9 | 82% |
| 50 mg/kg | 4 | 7 | 64% |
| 170 mg/kg | 4 | 7 | 64% |

Tumor Response

Tumor response was evaluated slightly differently from proposed. As we start shortly after tumor induction, shrinkage of the tumor compared to before treatment cannot be made. Next to that, we did not observe a tumor size reduction after initial outgrowth. So during the experimental time-frame outgrowth (progressive disease, PD) and tumor response (TR, growth delay till day 20) was evaluated. In Table 3 response rates are depicted.

Toxicity

Figure 5:
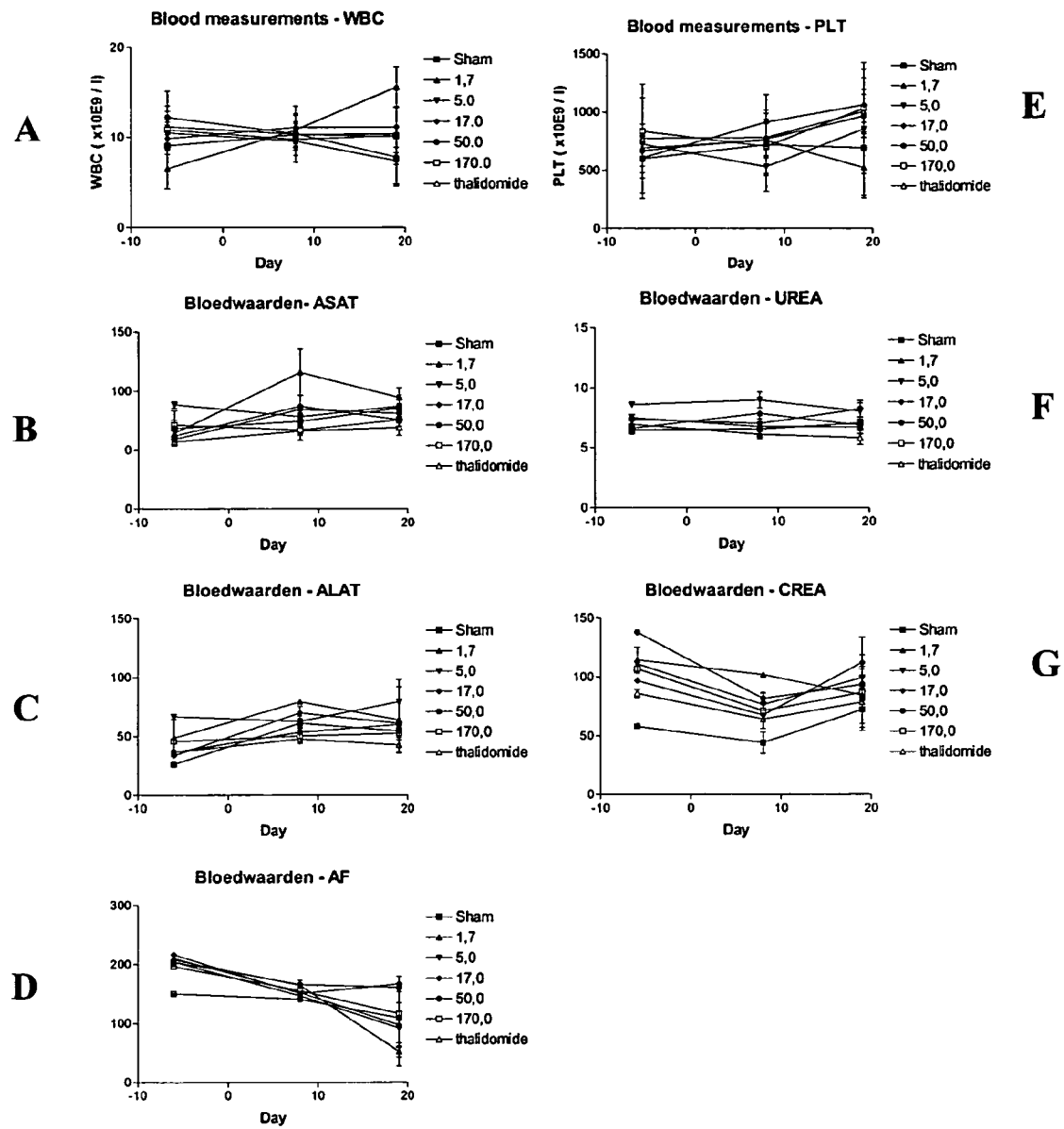
FIG. 5. During the escalating dose experiment toxicity of LQGV (SEQ ID NO:1) was evaluated by evaluation of blood markers for kidney and liver function and leukocyte count.
Figure 6:
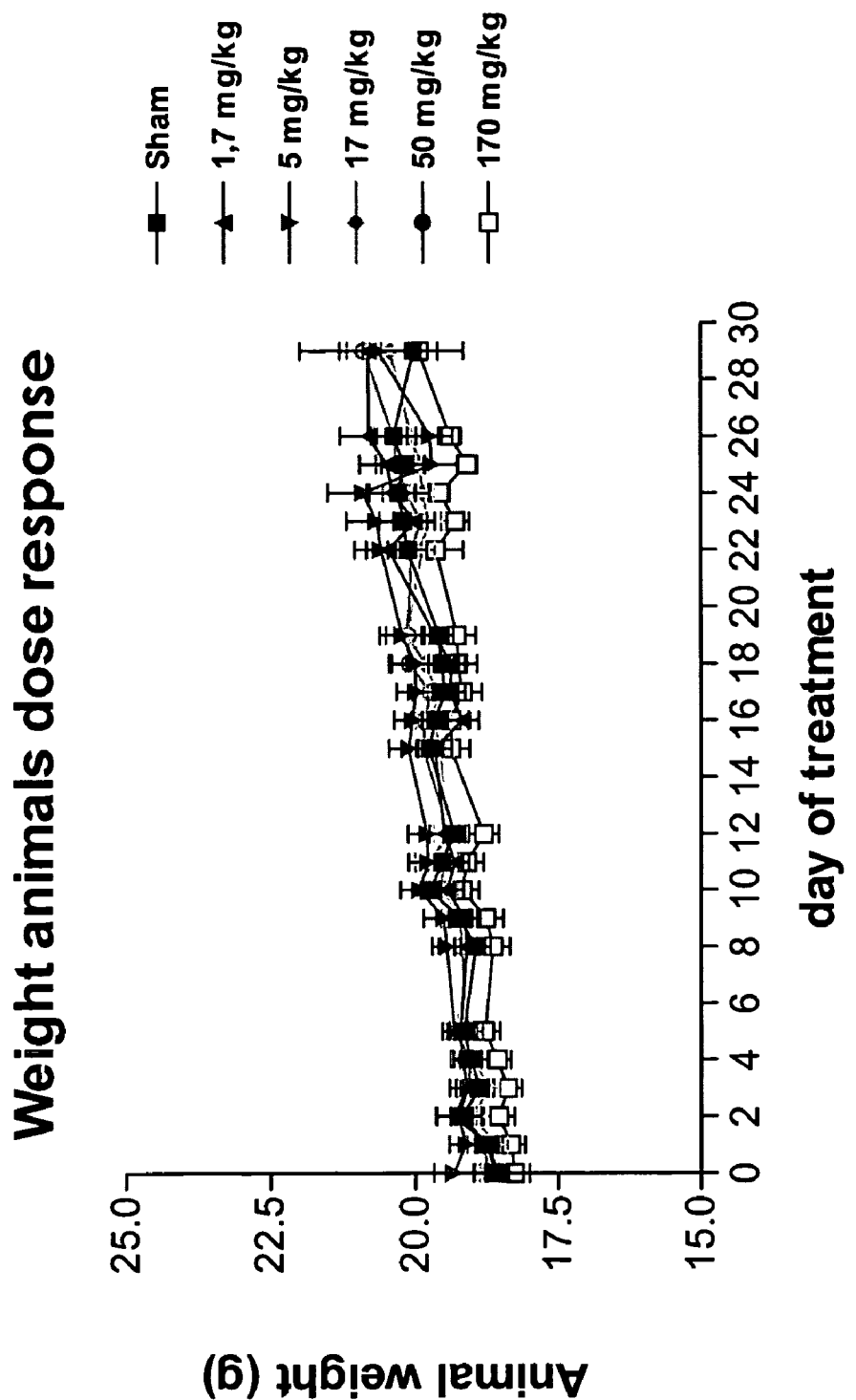
FIG. 6. During the escalating dose experiment toxicity of LQGV (SEQ ID NO:1) was evaluated by monitoring of animal weight.

During the experiment toxicity of the administered peptides was evaluated by monitoring of animal weight (FIG. 6) and by evaluation of blood markers for kidney and liver function and leukocyte count (FIG. 5). At all doses, no effect on animal weight was observed. Administration of the peptides had no effect on leukocyte number and did not affect the liver and kidney parameters. It is important to compare not only between the groups but also within the groups between individual mice. These results show no effect of peptide administration on all parameters tested.

Example IV

To further study anti-cell cycle activity of various oligopeptides a proliferation experiment in *Arabidopsis thaliana* seedlings was performed. The aim was to test a group of 140 oligopeptides of varying length for their effect on plant marker gene expression during rapid growth when avid cell division occurs. Both marker genes are related to the cell-cycle process, wherein high marker activity reflects a high cell-cycle activity and no marker activity reflects no cell-cycle activity and hence no proliferation.

Method

The peptides were re-suspended in 1× Phosphate Buffer Saline (PBS) pH8 to a final concentration of 5 mg/ml. The obtained solutions were then divided through 96-well round bottom plates (Corning Incorporated) at 40 microl per well. Plates were stored before use at −200C for four days. Seeds of *Arabidopsis thaliana* ecotype Ws-0 were surface sterilized in 2% commercial bleach (Glorix) for ten minutes and washed five times with sterile MQ water. The seeds were then re-suspended with 0.1% agar and plated on MS20 plates supplemented with 80 mg/l Kanamycin.

The plates were placed at 40° C. for two nights, and then transferred to a climate room at 210° C. and a 16/8 hours photoperiod. After four days of growth, the seedlings were transferred to 96-well plates containing the peptide solutions (four seedlings per well) and incubated for four and eight hours.

For this experiment, *Arabidopsis* homozygous seedlings harbouring two reporter genes fused to GUS were used. The first reporter gene used was a cell cycle marker, pCDG (Carmona et al., *The Plant Journal*, 1999, 20(4), 503-508), and the second an auxin responsive marker, DR5::GUS (Ulmasov et al., *The Plant Cell*, Vol. 9, 1963-1971). After incubation with the compounds, the seedlings were stained for GUS. The staining reaction was performed in 100 mM sodium phosphate buffer (pH 7.0) that contained 10 mM EDTA, 10% DMSO, 0.1% Triton X-100, 2 mM X-Gluc, 0.5 mM $K_3Fe(CN)_6$ and 0.5 mM $K_4Fe(CN)_6$ at 37° C. for 16 hours. To stop the GUS reaction and removed chlorophyll, the seedlings were treated for one hour with 96% ethanol and then stored in 70% ethanol. Stained seedlings were observed under a stereomicroscope and slides were made with seedlings showing an effect of the compound treatment. Seedlings were fixed and cleared in chloral hydrate solution for detailed microscopic observation and photography under a microscope equipped with DIC optics.

Results

Peptides were tested for an effect on marker gene expression on rapidly growing *Arabidopsis* young seedlings. This was monitored by changes on GUS distribution in different organs: root, root-hypocotyl transition zone and cotyledons.

From the 140 compounds tested, a total of 43 showed a clear effect on the expression of both markers tested. Surprisingly, the effects were clearly related to the length of the various peptides tested. As can be seen in Table 4 below, anti-cell cycle activity was over-represented in the short peptides, none of the peptides longer than nine amino acids gave reduction of cell cycle activity. Of the peptides of five to nine amino acids in length, about 22% showed reduction, but of the trimers and tetramers tested more than 50% showed reduction of cell cycle activity.

TABLE 4

Frequency distribution of peptides tested positive/peptide length as found in cell cycle test in *Arabidopsis thaliana*.

|    | #AA |    |    |    |    |    |    |    |    |    |    |
|----|-----|-----|-----|-----|-----|-----|-----|-----|-----|-----|-----|
|    | 3   | 4   | 5   | 6   | 7   | 8   | 9   | 10  | 12  | 13  | >14 |
| #  | 6   | 65  | 9   | 11  | 10  | 2   | 17  | 7   | 3   | 5   | 5   |
| #+ | 3   | 38  | 3   | 3   | 3   | 1   | 1   | 0   | 0   | 0   | 0   |
| %+ | 50% | 58% | 33% | 27% | 30% | 50% | 6%  | 0%  | 0%  | 0%  | 0%  |

AA = peptide length in amino acids;
# = number tested;
+ = number found positive;
%+ = percentage positive Results From cell-cycle studies in plants and in vivo reduction of tumor growth in mice cells, useful 3-mer peptides for treatment of cancer were identified, VVC, LAG, AQG. Similarly, useful 4-mer peptides for treatment of cancer are LQGV (SEQ ID NO:1), QVVC (SEQ ID NO:5), MTRV (SEQ ID NO:6), AQGV (SEQ ID NO:2), LAGV (SEQ ID NO:3), LQAV (SEQ ID NO:7), PGCP (SEQ ID NO:8), VGQL (SEQ ID NO:9), RVLQ (SEQ ID NO:10), EMFQ (SEQ ID NO:11), AVAL (SEQ ID NO:12), FVLS (SEQ ID NO:13), NMWD (SEQ ID NO:14), LCFL (SEQ ID NO:15), FSYA (SEQ ID NO:16), FWVD (SEQ ID NO:17), AFTV (SEQ ID NO:18), LGTL (SEQ ID NO:19), QLLG (SEQ ID NO:20), YAIT (SEQ ID NO:21), APSL (SEQ ID NO:22), ITTL (SEQ ID NO:23), QALG (SEQ ID NO:24), GVLC (SEQ ID NO:25), NLIN (SEQ ID NO:26), SPIE (SEQ ID NO:27), LNTI (SEQ ID NO:28), LHNL (SEQ ID NO:29), CPVQ (SEQ ID NO:30), EVVR (SEQ ID NO:31), MTEV (SEQ ID NO:32), EALE (SEQ ID NO:33), cancer are TLAVE (SEQ ID NO:38), VEGNL (SEQ ID NO:39), LNEAL (SEQ ID NO:40), useful 6-mer peptides for treatment of cancer are VLPALP (SEQ ID NO:4), MGGTWA (SEQ ID NO:41), LTCDDP (SEQ ID NO:42), useful 7-mer peptides for treatment of cancer are VLPALPQ (SEQ ID NO:43), VCNYRDV (SEQ ID NO:44), CPRGVNP (SEQ ID NO:45), a useful 8-mer peptide for treatment of cancer is QPLAPLVG (SEQ ID NO:46), and a useful 9-mer peptide for treatment of cancer is DINGFLPAL (SEQ ID NO:47).

What is claimed is:

1. A method of treating a subject suffering from lung cancer, said method comprising:
providing the subject with repeated administrations of LQGV (SEQ ID NO:1), or an acceptable salt thereof, wherein each repeated administration comprises a dose of at least 5 mg peptide/kg bodyweight of the subject,
thus treating the subject suffering from lung cancer.

2. The method according to claim 1, wherein each repeated administration of LQGV (SEQ ID NO:1) comprises a dose of at least 50 mg LQGV (SEQ ID NO:1) peptide/kg bodyweight of a subject.

3. The method according to claim 1, wherein the repeated administrations comprises three weekly administrations.

4. A method of treating a subject suffering from lung cancer, the method comprising:
administering to the subject a peptide, or acceptable salt of the peptide, wherein the peptide is LQGV (SEQ ID NO:1); and
providing the subject with a repeated administration of the peptide or acceptable salt of the peptide at a dose of at least 5 mg peptide/kg bodyweight of the subject,
thus treating the subject suffering from lung cancer.

5. The method according to claim 4, further comprising providing the subject with a repeated administration of the peptide at a dose of at least 50 mg peptide/kg bodyweight of a subject.

6. A method of treating a subject suffering from lung cancer, the method comprising:

administering to the subject a peptide or acceptable salt of the peptide, wherein the peptide is SEQ ID NO:1, thus treating the subject suffering from lung cancer.

* * * * *

UNITED STATES PATENT AND TRADEMARK OFFICE
CERTIFICATE OF CORRECTION

PATENT NO. : 7,662,776 B2
APPLICATION NO. : 11/481423
DATED : February 16, 2010
INVENTOR(S) : Nisar A. Khan et al.

It is certified that error appears in the above-identified patent and that said Letters Patent is hereby corrected as shown below:

On the title page:
In ITEM (57) ABSTRACT
Page 1, 2$^{nd}$ column, line 16    change "NO:), MTRV"
to --NO:5), MTRV--

Signed and Sealed this
Ninth Day of April, 2013

Teresa Stanek Rea
*Acting Director of the United States Patent and Trademark Office*

SEQUENCE LISTING

```
<160> NUMBER OF SEQ ID NOS: 68

<210> SEQ ID NO 1
<211> LENGTH: 4
<212> TYPE: PRT
<213> ORGANISM: Artificial
<220> FEATURE:
<223> OTHER INFORMATION: Chemically synthesized antitumor peptide LQGV

<400> SEQUENCE: 1

Leu Gln Gly Val
1

<210> SEQ ID NO 2
<211> LENGTH: 4
<212> TYPE: PRT
<213> ORGANISM: Artificial
<220> FEATURE:
<223> OTHER INFORMATION: Chemically synthesized antitumor peptide AQGV

<400> SEQUENCE: 2

Ala Gln Gly Val
1

<210> SEQ ID NO 3
<211> LENGTH: 4
<212> TYPE: PRT
<213> ORGANISM: Artificial
<220> FEATURE:
<223> OTHER INFORMATION: Chemically synthesized antitumor peptide LAGV

<400> SEQUENCE: 3
```

```
Leu Ala Gly Val
1

<210> SEQ ID NO 4
<211> LENGTH: 6
<212> TYPE: PRT
<213> ORGANISM: Artificial
<220> FEATURE:
<223> OTHER INFORMATION: Chemically synthesized antitumor peptide VLPALP

<400> SEQUENCE: 4

Val Leu Pro Ala Leu Pro
1               5

<210> SEQ ID NO 5
<211> LENGTH: 4
<212> TYPE: PRT
<213> ORGANISM: Artificial
<220> FEATURE:
<223> OTHER INFORMATION: Chemically synthesized antitumor peptide QVVC

<400> SEQUENCE: 5

Gln Val Val Cys
1

<210> SEQ ID NO 6
<211> LENGTH: 4
<212> TYPE: PRT
<213> ORGANISM: Artificial
<220> FEATURE:
<223> OTHER INFORMATION: Chemically synthesized antitumor peptide MTRV

<400> SEQUENCE: 6

Met Thr Arg Val
1

<210> SEQ ID NO 7
<211> LENGTH: 4
<212> TYPE: PRT
<213> ORGANISM: Artificial
<220> FEATURE:
<223> OTHER INFORMATION: Chemically synthesized antitumor peptide LQAV

<400> SEQUENCE: 7

Leu Gln Ala Val
1

<210> SEQ ID NO 8
<211> LENGTH: 4
<212> TYPE: PRT
<213> ORGANISM: Artificial
<220> FEATURE:
<223> OTHER INFORMATION: Chemically synthesized antitumor peptide PGCP

<400> SEQUENCE: 8

Pro Gly Cys Pro
1

<210> SEQ ID NO 9
<211> LENGTH: 4
<212> TYPE: PRT
<213> ORGANISM: Artificial
<220> FEATURE:
<223> OTHER INFORMATION: Chemically synthesized antitumor peptide VGQL

<400> SEQUENCE: 9

Val Gly Gln Leu
```

-continued

```
<210> SEQ ID NO 10
<211> LENGTH: 4
<212> TYPE: PRT
<213> ORGANISM: Artificial
<220> FEATURE:
<223> OTHER INFORMATION: Chemically synthesized antitumor peptide RVLQ

<400> SEQUENCE: 10

Arg Val Leu Gln
1

<210> SEQ ID NO 11
<211> LENGTH: 4
<212> TYPE: PRT
<213> ORGANISM: Artificial
<220> FEATURE:
<223> OTHER INFORMATION: Chemically synthesized antitumor peptide EMFQ

<400> SEQUENCE: 11

Glu Met Phe Gln
1

<210> SEQ ID NO 12
<211> LENGTH: 4
<212> TYPE: PRT
<213> ORGANISM: Artificial
<220> FEATURE:
<223> OTHER INFORMATION: Chemically synthesized antitumor peptide AVAL

<400> SEQUENCE: 12

Ala Val Ala Leu
1

<210> SEQ ID NO 13
<211> LENGTH: 4
<212> TYPE: PRT
<213> ORGANISM: Artificial
<220> FEATURE:
<223> OTHER INFORMATION: Chemically synthesized antitumor peptide FVLS

<400> SEQUENCE: 13

Phe Val Leu Ser
1

<210> SEQ ID NO 14
<211> LENGTH: 4
<212> TYPE: PRT
<213> ORGANISM: Artificial
<220> FEATURE:
<223> OTHER INFORMATION: Chemically synthesized antitumor peptide NMWD

<400> SEQUENCE: 14

Asn Met Trp Asp
1

<210> SEQ ID NO 15
<211> LENGTH: 4
<212> TYPE: PRT
<213> ORGANISM: Artificial
<220> FEATURE:
<223> OTHER INFORMATION: Chemically synthesized antitumor peptide LCFL

<400> SEQUENCE: 15

Leu Cys Phe Leu
1
```

-continued

```
<210> SEQ ID NO 16
<211> LENGTH: 4
<212> TYPE: PRT
<213> ORGANISM: Artificial
<220> FEATURE:
<223> OTHER INFORMATION: Chemically synthesized antitumor peptide FSYA

<400> SEQUENCE: 16

Phe Ser Tyr Ala
1

<210> SEQ ID NO 17
<211> LENGTH: 4
<212> TYPE: PRT
<213> ORGANISM: Artificial
<220> FEATURE:
<223> OTHER INFORMATION: Chemically synthesized antitumor peptide FWVD

<400> SEQUENCE: 17

Phe Trp Val Asp
1

<210> SEQ ID NO 18
<211> LENGTH: 4
<212> TYPE: PRT
<213> ORGANISM: Artificial
<220> FEATURE:
<223> OTHER INFORMATION: Chemically synthesized antitumor peptide AFTV

<400> SEQUENCE: 18

Ala Phe Thr Val
1

<210> SEQ ID NO 19
<211> LENGTH: 4
<212> TYPE: PRT
<213> ORGANISM: Artificial
<220> FEATURE:
<223> OTHER INFORMATION: Chemically synthesized antitumor peptide LGTL

<400> SEQUENCE: 19

Leu Gly Thr Leu
1

<210> SEQ ID NO 20
<211> LENGTH: 4
<212> TYPE: PRT
<213> ORGANISM: Artificial
<220> FEATURE:
<223> OTHER INFORMATION: Chemically synthesized antitumor peptide QLLG

<400> SEQUENCE: 20

Gln Leu Leu Gly
1

<210> SEQ ID NO 21
<211> LENGTH: 4
<212> TYPE: PRT
<213> ORGANISM: Artificial
<220> FEATURE:
<223> OTHER INFORMATION: Chemically synthesized antitumor peptide YAIT

<400> SEQUENCE: 21

Tyr Ala Ile Thr
1
```

```
<210> SEQ ID NO 22
<211> LENGTH: 4
<212> TYPE: PRT
<213> ORGANISM: Artificial
<220> FEATURE:
<223> OTHER INFORMATION: Chemically synthesized antitumor peptide APSL

<400> SEQUENCE: 22

Ala Pro Ser Leu
1

<210> SEQ ID NO 23
<211> LENGTH: 4
<212> TYPE: PRT
<213> ORGANISM: Artificial
<220> FEATURE:
<223> OTHER INFORMATION: Chemically synthesized antitumor peptide ITTL

<400> SEQUENCE: 23

Ile Thr Thr Leu
1

<210> SEQ ID NO 24
<211> LENGTH: 4
<212> TYPE: PRT
<213> ORGANISM: Artificial
<220> FEATURE:
<223> OTHER INFORMATION: Chemically synthesized antitumor peptide QALG

<400> SEQUENCE: 24

Gln Ala Leu Gly
1

<210> SEQ ID NO 25
<211> LENGTH: 4
<212> TYPE: PRT
<213> ORGANISM: Artificial
<220> FEATURE:
<223> OTHER INFORMATION: Chemically synthesized antitumor peptide GVLC

<400> SEQUENCE: 25

Gly Val Leu Cys
1

<210> SEQ ID NO 26
<211> LENGTH: 4
<212> TYPE: PRT
<213> ORGANISM: Artificial
<220> FEATURE:
<223> OTHER INFORMATION: Chemically synthesized antitumor peptide NLIN

<400> SEQUENCE: 26

Asn Leu Ile Asn
1

<210> SEQ ID NO 27
<211> LENGTH: 4
<212> TYPE: PRT
<213> ORGANISM: Artificial
<220> FEATURE:
<223> OTHER INFORMATION: Chemically synthesized antitumor peptide SPIE

<400> SEQUENCE: 27

Ser Pro Ile Glu
1
```

```
<210> SEQ ID NO 28
<211> LENGTH: 4
<212> TYPE: PRT
<213> ORGANISM: Artificial
<220> FEATURE:
<223> OTHER INFORMATION: Chemically synthesized antitumor peptide LNTI

<400> SEQUENCE: 28

Leu Asn Thr Ile
1

<210> SEQ ID NO 29
<211> LENGTH: 4
<212> TYPE: PRT
<213> ORGANISM: Artificial
<220> FEATURE:
<223> OTHER INFORMATION: Chemically synthesized antitumor peptide LHNL

<400> SEQUENCE: 29

Leu His Asn Leu
1

<210> SEQ ID NO 30
<211> LENGTH: 4
<212> TYPE: PRT
<213> ORGANISM: Artificial
<220> FEATURE:
<223> OTHER INFORMATION: Chemically synthesized antitumor peptide CPVQ

<400> SEQUENCE: 30

Cys Pro Val Gln
1

<210> SEQ ID NO 31
<211> LENGTH: 4
<212> TYPE: PRT
<213> ORGANISM: Artificial
<220> FEATURE:
<223> OTHER INFORMATION: Chemically synthesized antitumor peptide EVVR

<400> SEQUENCE: 31

Glu Val Val Arg
1

<210> SEQ ID NO 32
<211> LENGTH: 4
<212> TYPE: PRT
<213> ORGANISM: Artificial
<220> FEATURE:
<223> OTHER INFORMATION: Chemically synthesized antitumor peptide MTEV

<400> SEQUENCE: 32

Met Thr Glu Val
1

<210> SEQ ID NO 33
<211> LENGTH: 4
<212> TYPE: PRT
<213> ORGANISM: Artificial
<220> FEATURE:
<223> OTHER INFORMATION: Chemically synthesized antitumor peptide EALE

<400> SEQUENCE: 33

Glu Ala Leu Glu
1

<210> SEQ ID NO 34
```

```
<211> LENGTH: 4
<212> TYPE: PRT
<213> ORGANISM: Artificial
<220> FEATURE:
<223> OTHER INFORMATION: Chemically synthesized antitumor peptide EPPE

<400> SEQUENCE: 34

Glu Pro Pro Glu
1

<210> SEQ ID NO 35
<211> LENGTH: 4
<212> TYPE: PRT
<213> ORGANISM: Artificial
<220> FEATURE:
<223> OTHER INFORMATION: Chemically synthesized antitumor peptide VGGI

<400> SEQUENCE: 35

Val Gly Gly Ile
1

<210> SEQ ID NO 36
<211> LENGTH: 4
<212> TYPE: PRT
<213> ORGANISM: Artificial
<220> FEATURE:
<223> OTHER INFORMATION: Chemically synthesized antitumor peptide RLPG

<400> SEQUENCE: 36

Arg Leu Pro Gly
1

<210> SEQ ID NO 37
<211> LENGTH: 4
<212> TYPE: PRT
<213> ORGANISM: Artificial
<220> FEATURE:
<223> OTHER INFORMATION: Chemically synthesized antitumor peptide LQGA

<400> SEQUENCE: 37

Leu Gln Gly Ala
1

<210> SEQ ID NO 38
<211> LENGTH: 5
<212> TYPE: PRT
<213> ORGANISM: Artificial
<220> FEATURE:
<223> OTHER INFORMATION: Chemically synthesized antitumor peptide TLAVE

<400> SEQUENCE: 38

Thr Leu Ala Val Glu
1               5

<210> SEQ ID NO 39
<211> LENGTH: 5
<212> TYPE: PRT
<213> ORGANISM: Artificial
<220> FEATURE:
<223> OTHER INFORMATION: Chemically synthesized antitumor peptide VEGNL

<400> SEQUENCE: 39

Val Glu Gly Asn Leu
1               5

<210> SEQ ID NO 40
<211> LENGTH: 5
```

```
<212> TYPE: PRT
<213> ORGANISM: Artificial
<220> FEATURE:
<223> OTHER INFORMATION: Chemically synthesized antitumor peptide LNEAL

<400> SEQUENCE: 40

Leu Asn Glu Ala Leu
1               5

<210> SEQ ID NO 41
<211> LENGTH: 6
<212> TYPE: PRT
<213> ORGANISM: Artificial
<220> FEATURE:
<223> OTHER INFORMATION: Chemically synthesized antitumor peptide MGGTWA

<400> SEQUENCE: 41

Met Gly Gly Thr Trp Ala
1               5

<210> SEQ ID NO 42
<211> LENGTH: 6
<212> TYPE: PRT
<213> ORGANISM: Artificial
<220> FEATURE:
<223> OTHER INFORMATION: Chemically synthesized antitumor peptide LTCDDP

<400> SEQUENCE: 42

Leu Thr Cys Asp Asp Pro
1               5

<210> SEQ ID NO 43
<211> LENGTH: 7
<212> TYPE: PRT
<213> ORGANISM: Artificial
<220> FEATURE:
<223> OTHER INFORMATION: Chemically synthesized antitumor peptide
      VLPALPQ

<400> SEQUENCE: 43

Val Leu Pro Ala Leu Pro Gln
1               5

<210> SEQ ID NO 44
<211> LENGTH: 7
<212> TYPE: PRT
<213> ORGANISM: Artificial
<220> FEATURE:
<223> OTHER INFORMATION: Chemically synthesized antitumor peptide
      VCNYRDV

<400> SEQUENCE: 44

Val Cys Asn Tyr Arg Asp Val
1               5

<210> SEQ ID NO 45
<211> LENGTH: 7
<212> TYPE: PRT
<213> ORGANISM: Artificial
<220> FEATURE:
<223> OTHER INFORMATION: Chemically synthesized antitumor peptide
      CPRGVNP

<400> SEQUENCE: 45

Cys Pro Arg Gly Val Asn Pro
1               5
```

```
<210> SEQ ID NO 46
<211> LENGTH: 8
<212> TYPE: PRT
<213> ORGANISM: Artificial
<220> FEATURE:
<223> OTHER INFORMATION: Chemically synthesized antitumor peptide
      QPLAPLVG

<400> SEQUENCE: 46

Gln Pro Leu Ala Pro Leu Val Gly
1               5

<210> SEQ ID NO 47
<211> LENGTH: 9
<212> TYPE: PRT
<213> ORGANISM: Artificial
<220> FEATURE:
<223> OTHER INFORMATION: Chemically synthesized antitumor peptide
      DINGFLPAL

<400> SEQUENCE: 47

Asp Ile Asn Gly Phe Leu Pro Ala Leu
1               5

<210> SEQ ID NO 48
<211> LENGTH: 17
<212> TYPE: PRT
<213> ORGANISM: Artificial
<220> FEATURE:
<223> OTHER INFORMATION: Chemically synthesized antitumor peptide
      MTRVLQGVLPALPQVVC

<400> SEQUENCE: 48

Met Thr Arg Val Leu Gln Gly Val Leu Pro Ala Leu Pro Gln Val Val
1               5                   10                  15

Cys

<210> SEQ ID NO 49
<211> LENGTH: 4
<212> TYPE: PRT
<213> ORGANISM: Artificial
<220> FEATURE:
<223> OTHER INFORMATION: Chemically synthesized antitumor peptide
      XXXX - 1
<220> FEATURE:
<221> NAME/KEY: VARIANT
<222> LOCATION: (1)..(1)
<223> OTHER INFORMATION: X is Ala or Leu
<220> FEATURE:
<221> NAME/KEY: VARIANT
<222> LOCATION: (2)..(2)
<223> OTHER INFORMATION: X is Glu, Pro or Ala
<220> FEATURE:
<221> NAME/KEY: VARIANT
<222> LOCATION: (3)..(3)
<223> OTHER INFORMATION: X is Gly
<220> FEATURE:
<221> NAME/KEY: VARIANT
<222> LOCATION: (4)..(4)
<223> OTHER INFORMATION: X is Val or Ala

<400> SEQUENCE: 49

Xaa Xaa Xaa Xaa
1

<210> SEQ ID NO 50
<211> LENGTH: 6
<212> TYPE: PRT
<213> ORGANISM: Artificial
<220> FEATURE:
```

```
<223> OTHER INFORMATION: Chemically synthesized antitumor peptide XXPAXX
<220> FEATURE:
<221> NAME/KEY: VARIANT
<222> LOCATION: (1)..(1)
<223> OTHER INFORMATION: X is Val or Ala
<220> FEATURE:
<221> NAME/KEY: VARIANT
<222> LOCATION: (2)..(5)
<223> OTHER INFORMATION: X on position 2 and 5 is Leu or Ala
<220> FEATURE:
<221> NAME/KEY: VARIANT
<222> LOCATION: (6)..(6)
<223> OTHER INFORMATION: X is Pro or Ala

<400> SEQUENCE: 50

Xaa Xaa Pro Ala Xaa Xaa
1               5

<210> SEQ ID NO 51
<211> LENGTH: 6
<212> TYPE: PRT
<213> ORGANISM: Artificial
<220> FEATURE:
<223> OTHER INFORMATION: Chemically synthesized antitumor peptide ALPALP

<400> SEQUENCE: 51

Ala Leu Pro Ala Leu Pro
1               5

<210> SEQ ID NO 52
<211> LENGTH: 6
<212> TYPE: PRT
<213> ORGANISM: Artificial
<220> FEATURE:
<223> OTHER INFORMATION: Chemically synthesized antitumor peptide VAPALP

<400> SEQUENCE: 52

Val Ala Pro Ala Leu Pro
1               5

<210> SEQ ID NO 53
<211> LENGTH: 7
<212> TYPE: PRT
<213> ORGANISM: Artificial
<220> FEATURE:
<223> OTHER INFORMATION: Chemically synthesized antitumor peptide
      ALPALPQ

<400> SEQUENCE: 53

Ala Leu Pro Ala Leu Pro Gln
1               5

<210> SEQ ID NO 54
<211> LENGTH: 7
<212> TYPE: PRT
<213> ORGANISM: Artificial
<220> FEATURE:
<223> OTHER INFORMATION: Chemically synthesized antitumor peptide
      VLPAAPQ

<400> SEQUENCE: 54

Val Leu Pro Ala Ala Pro Gln
1               5

<210> SEQ ID NO 55
<211> LENGTH: 7
<212> TYPE: PRT
<213> ORGANISM: Artificial
<220> FEATURE:
```

```
<223> OTHER INFORMATION: Chemically synthesized antitumor peptide
      VLPALAQ

<400> SEQUENCE: 55

Val Leu Pro Ala Leu Ala Gln
1               5

<210> SEQ ID NO 56
<211> LENGTH: 6
<212> TYPE: PRT
<213> ORGANISM: Artificial
<220> FEATURE:
<223> OTHER INFORMATION: Chemically synthesized antitumor peptide VLPALA

<400> SEQUENCE: 56

Val Leu Pro Ala Leu Ala
1               5

<210> SEQ ID NO 57
<211> LENGTH: 7
<212> TYPE: PRT
<213> ORGANISM: Artificial
<220> FEATURE:
<223> OTHER INFORMATION: Chemically synthesized antitumor peptide
      VLPALPA

<400> SEQUENCE: 57

Val Leu Pro Ala Leu Pro Ala
1               5

<210> SEQ ID NO 58
<211> LENGTH: 7
<212> TYPE: PRT
<213> ORGANISM: Artificial
<220> FEATURE:
<223> OTHER INFORMATION: Chemically synthesized antitumor peptide
      GVLPALP

<400> SEQUENCE: 58

Gly Val Leu Pro Ala Leu Pro
1               5

<210> SEQ ID NO 59
<211> LENGTH: 6
<212> TYPE: PRT
<213> ORGANISM: Artificial
<220> FEATURE:
<223> OTHER INFORMATION: Chemically synthesized antitumor peptide VLAALP

<400> SEQUENCE: 59

Val Leu Ala Ala Leu Pro
1               5

<210> SEQ ID NO 60
<211> LENGTH: 4
<212> TYPE: PRT
<213> ORGANISM: Artificial
<220> FEATURE:
<223> OTHER INFORMATION: Chemically synthesized antitumor peptide
      XXXX - 2
<220> FEATURE:
<221> NAME/KEY: VARIANT
<222> LOCATION: (1)..(1)
<223> OTHER INFORMATION: X is Ala, Leu or Met
<220> FEATURE:
<221> NAME/KEY: VARIANT
<222> LOCATION: (2)..(2)
<223> OTHER INFORMATION: X is Gln, Thr, Ala or Pro
<220> FEATURE:
```

```
<221> NAME/KEY: VARIANT
<222> LOCATION: (3)..(3)
<223> OTHER INFORMATION: X is Gly or Arg
<220> FEATURE:
<221> NAME/KEY: VARIANT
<222> LOCATION: (4)..(4)
<223> OTHER INFORMATION: X is Cys, Ala or Val

<400> SEQUENCE: 60

Xaa Xaa Xaa Xaa
1

<210> SEQ ID NO 61
<211> LENGTH: 4
<212> TYPE: PRT
<213> ORGANISM: Artificial
<220> FEATURE:
<223> OTHER INFORMATION: Chemically synthesized antitumor peptide LPGC

<400> SEQUENCE: 61

Leu Pro Gly Cys
1

<210> SEQ ID NO 62
<211> LENGTH: 7
<212> TYPE: PRT
<213> ORGANISM: Artificial
<220> FEATURE:
<223> OTHER INFORMATION: Chemically synthesized antitumor peptide
      VLAALPQ

<400> SEQUENCE: 62

Val Leu Ala Ala Leu Pro Gln
1               5

<210> SEQ ID NO 63
<211> LENGTH: 38
<212> TYPE: PRT
<213> ORGANISM: Artificial
<220> FEATURE:
<223> OTHER INFORMATION: Chemically synthesized antitumor peptide
      VVCNYRDVRFESIRLPGCPRGVNPVVSYAVALSCQCAL

<400> SEQUENCE: 63

Val Val Cys Asn Tyr Arg Asp Val Arg Phe Glu Ser Ile Arg Leu Pro
1               5                   10                  15

Gly Cys Pro Arg Gly Val Asn Pro Val Val Ser Tyr Ala Val Ala Leu
                20                  25                  30

Ser Cys Gln Cys Ala Leu
            35

<210> SEQ ID NO 64
<211> LENGTH: 35
<212> TYPE: PRT
<213> ORGANISM: Artificial
<220> FEATURE:
<223> OTHER INFORMATION: Chemically synthesized antitumor peptide
      RPRCRPINATLAVEKEGCPVCITVNTTICAGYCPT

<400> SEQUENCE: 64

Arg Pro Arg Cys Arg Pro Ile Asn Ala Thr Leu Ala Val Glu Lys Glu
1               5                   10                  15

Gly Cys Pro Val Cys Ile Thr Val Asn Thr Thr Ile Cys Ala Gly Tyr
                20                  25                  30

Cys Pro Thr
        35
```

```
<210> SEQ ID NO 65
<211> LENGTH: 18
<212> TYPE: PRT
<213> ORGANISM: Artificial
<220> FEATURE:
<223> OTHER INFORMATION: Chemically synthesized antitumor peptide
      SKAPPPSLPSPSRLPGPS

<400> SEQUENCE: 65

Ser Lys Ala Pro Pro Pro Ser Leu Pro Ser Pro Ser Arg Leu Pro Gly
1               5                   10                  15

Pro Ser

<210> SEQ ID NO 66
<211> LENGTH: 13
<212> TYPE: PRT
<213> ORGANISM: Artificial
<220> FEATURE:
<223> OTHER INFORMATION: Chemically synthesized antitumor peptide
      LQGVLPALPQVVC

<400> SEQUENCE: 66

Leu Gln Gly Val Leu Pro Ala Leu Pro Gln Val Val Cys
1               5                   10

<210> SEQ ID NO 67
<211> LENGTH: 16
<212> TYPE: PRT
<213> ORGANISM: Artificial
<220> FEATURE:
<223> OTHER INFORMATION: Chemically synthesized antitumor peptide
      SIRLPGCPRGVNPVVS

<400> SEQUENCE: 67

Ser Ile Arg Leu Pro Gly Cys Pro Arg Gly Val Asn Pro Val Val Ser
1               5                   10                  15

<210> SEQ ID NO 68
<211> LENGTH: 13
<212> TYPE: PRT
<213> ORGANISM: Artificial
<220> FEATURE:
<223> OTHER INFORMATION: Chemically synthesized antitumor peptide
      LPGCPRGVNPVVS

<400> SEQUENCE: 68

Leu Pro Gly Cys Pro Arg Gly Val Asn Pro Val Val Ser
1               5                   10
```